(12) United States Patent
Gorfinkel et al.

(10) Patent No.: US 8,304,712 B2
(45) Date of Patent: Nov. 6, 2012

(54) LIGHT FOCUSING IN LINEAR CHANNEL ARRAYS

(75) Inventors: Vera Gorfinkel, Stony Brook, NY (US); Michael Gorbovitski, Stony Brook, NY (US); Andriy Tsupryk, Coram, NY (US)

(73) Assignee: The Research Foundation of State University of New York, Albany, NY (US)

( * ) Notice: Subject to any disclaimer, the term of this patent is extended or adjusted under 35 U.S.C. 154(b) by 633 days.

(21) Appl. No.: 11/989,788

(22) PCT Filed: Aug. 11, 2006

(86) PCT No.: PCT/US2006/031363
§ 371 (c)(1),
(2), (4) Date: Mar. 2, 2010

(87) PCT Pub. No.: WO2007/021925
PCT Pub. Date: Feb. 22, 2007

(65) Prior Publication Data
US 2010/0163715 A1    Jul. 1, 2010

Related U.S. Application Data

(60) Provisional application No. 60/707,664, filed on Aug. 12, 2005.

(51) Int. Cl.
*G01D 5/30* (2006.01)
*G02B 27/12* (2006.01)
*G06F 17/10* (2006.01)
*G01N 21/05* (2006.01)

(52) U.S. Cl. ........ 250/227.28; 359/639; 703/2; 356/246

(58) Field of Classification Search ............. 250/227.28; 359/639; 703/2; 356/246
See application file for complete search history.

(56) References Cited

U.S. PATENT DOCUMENTS

| | | | | |
|---|---|---|---|---|
| 6,731,437 | B2 * | 5/2004 | Carrillo | 359/796 |
| 6,888,628 | B2 * | 5/2005 | Carrillo | 356/246 |
| 2002/0110839 | A1 * | 8/2002 | Bach et al. | 435/7.9 |
| 2002/0162746 | A1 * | 11/2002 | Carrillo | 204/452 |
| 2004/0169931 | A1 * | 9/2004 | Carrillo | 359/642 |

* cited by examiner

*Primary Examiner* — Seung C Sohn
(74) *Attorney, Agent, or Firm* — Medlen & Carroll, LLP

(57) ABSTRACT

The invention relates to devices that contain linear channels having optically transparent substances for focusing light. In some embodiments, the invention relates to improved nucleic acid sequencing methods using devices disclosed herein. In other embodiments, the invention relates to the arrangement of materials in and around capillary tubes with refractive indexes that maximize the number of channels useful for fluorescent detection of compositions after capillary electrophoresis.

32 Claims, 36 Drawing Sheets

# LIGHT FOCUSING IN LINEAR CHANNEL ARRAYS

CROSS-REFERENCE TO RELATED APPLICATION

This application claims the benefit of provisional U.S. Appln. No. 60/707,664, filed Aug. 12, 2005, incorporated herein in its entirety.

FIELD OF INVENTION

The invention relates to devices that contain linearly aligned channels comprising optically transparent elements comprising substances or materials for transmitting and focusing light. In some embodiments, the invention relates to improved nucleic acid sequencing methods using devices disclosed herein. In other embodiments, the invention relates to the arrangement of materials in and around capillary tubes, the materials having refractive indexes that maximize the number of channels useful for fluorescent detection of compositions after capillary electrophoresis.

BACKGROUND

In linear multicapillary array-based DNA sequencing machines, a laser beam irradiates individual capillaries of the array, and a multipixel photodetector collects the resulting fluorescence of fluorophore-labeled DNA fragments in the capillaries. Increasing the number of simultaneously operated capillary lanes can significantly increase the throughput of DNA sequencing machines. Side-irradiation or -illumination of linearly arrayed capillaries is convenient and is thus widely used in the design of modern sequencers. However, reflection and refraction of the laser beam at the walls of individual capillaries causes nonuniform illumination of the capillary channels. Thus, there is a need for devices and methods that maximize illumination but minimize reflection and refraction of the laser beam to maximize the number of capillaries that can be utilized.

SUMMARY OF INVENTION

The invention relates to devices that contain linearly aligned channels having optically transparent substances for focusing light. In some embodiments, the invention relates to improved nucleic acid sequencing methods using devices disclosed herein. In other embodiments, the invention relates to the arrangement of materials in and around capillary tubes, the materials having refractive indexes that maximize the number of channels useful for fluorescent detection of electrophoresed compositions in the capillaries. Importantly, these materials need not surround or cover the entire tube; each tube in the array may be surrounded only in the region where the laser light will make contact with the tube. Regions of the tube not in the light path may or may not be filled with such materials. Regardless of the extent of coverage, these materials may be inserted into or fill spaces between tubes; alternatively, these materials may take the form of channels or even tubes. The materials, for best effect, are commingled with or positioned uniformly with respect to the capillary tubes; for example, in one embodiment, there is material between adjacent capillary tubes in the array. In one embodiment, there is material between every two capillary tubes in the array. In one embodiment, there is material between every three capillary tubes in the three dimensional array.

In some embodiments the invention relates to a linear multi-capillary array formed of active or working capillaries and, interposed therebetween, composite optical insertions. The array may be surrounded (or partially surrounded) by a transparent medium. The refractive index of at least one of the media that comprise the working capillaries is different from the refractive index of at least one of the media that comprise the composite optical insertions. In further embodiments, the refractive indices of said active capillaries, said composite insertions, and the medium surrounding the array in the region of the system's light-path or detection zone are selected so that they provide maximum (or at least improved) transmission of the laser beam through the linear multi-capillary array. In further embodiments, the refractive indices of the linear multi-capillary array capillaries, the outer layer of each of the composite insertions, and the surrounding media are such that they form an optically homogeneous system, and the refractive index and the shape of the inner regions bounded by the outer layer of the composite insertions are such that they enable a guiding of the illumination beam through the linear multi-capillary array with maximum transmittance coefficient.

In additional embodiments, the invention relates to a laser illumination and fluorescence collection system comprising a capillary array with composite insertions, image transmitting fiber array, and multi-channel photodetector. In other embodiments said system further comprises high-aperture projection optics.

In other embodiments, the invention relates to an array etched on a glass chip (refractive index $n_2$) comprising working channels filled with polymer (refractive index $n_3$) alternated by channels filled with a medium of refractive index $n'_3$ wherein $n'_3$ is greater than $n_2$ and $n'_3$ is greater than $n_3$. In further embodiments the absolute value of $n'_3$ minus $n_2$ is equal to the absolute value of $n_3$ minus $n_2$. In further embodiments, said array further comprises a cover wherein the channels etched in the glass chip are replicated such that the covered chip forms cylindrical channels, the cover being secured by applied pressure or compatible adhesive materials as is known in the art.

In additional embodiments, the invention relates to a laser illumination and fluorescence collection system comprising an etched-on-glass-chip capillary array with composite insertions as described herein, image transmitting fiber array, and multi-channel photodetector. In further embodiments, said system further comprises high-aperture projection optics. In further embodiments, said array comprises a flat cover. In further embodiments, the flat cover comprises at least two layers. In further embodiments, the cover provides total internal reflection of the laser illumination beam (if the beam is directed at the side of the array) from any point on its channel-facing surface. In further embodiments, the cover is a mirror. In further embodiments, the cover is a dielectric mirror.

In some embodiments, the invention relates to a laser illumination and fluorescence collection system comprising an etched-on-glass-chip capillary array with composite insertions as described herein, an image-transmitting fiber array, and a multi-channel photodetector. In further embodiments, said system further comprises high-aperture projection optics.

In some embodiments, the invention relates to a device comprising: i) a transparent material having a first refractive index comprising a) a first plurality of channels filled with a first transparent medium having a second refractive index and b) a second plurality of channels filled with a second medium having a third refractive index; ii) a laser; wherein said first and second plurality of channels, at least in the region of the laser's light-path, lie parallel to each other in a single plane, and perpendicular to said laser beam, the path of which beam also lies in said plane; wherein said third refractive index is greater than said first refractive index and said third refractive index is greater than said second refractive index. In further embodiments, the absolute value of said third refractive index minus said first refractive index is equal to the absolute value of said third refractive index minus said first refractive index. In further embodiments, said third refractive index is greater than fused quartz.

In additional embodiments, the invention relates to a device comprising: a first plurality of capillary tubes comprised of a first material having a first refractive index, a first medium having a second refractive index inside each member of said first plurality of capillary tubes, a second plurality of capillary tubes comprised of a second material having a third refractive index, a second medium having a fourth refractive index inside each member of said second plurality of capillary tubes, a compartment, a source of electromagnetic radiation, and a third medium having a fifth refractive index; wherein said first and second plurality of capillary tubes are contained in said compartment and said third medium is configured to surround the outside of said first and second plurality of capillary tubes (or at least surround the portions of these tubes in the light path); wherein said first plurality of capillary tubes and said second plurality of capillary tubes are configured in an alignment such that said electromagnetic radiation travels through said capillary tubes; wherein said first and third refractive index are equal; and wherein said fourth refractive index is greater than said first, third, and fifth refractive index. In some embodiments, said fifth refractive index is greater than 1.33. In further embodiments, said second refractive index is less that said first, third, and fifth refractive index. In further embodiments, said first and second materials are both fused quartz. In further embodiments, said first, third, and fifth refractive indices are equal. In further embodiments, said second refractive index is between 1.33 and 1.44, and said fourth refractive index is between 1.48 and 1.70. In further embodiments, the distance between the outside of said first plurality of capillary tubes and the outside of said second plurality of capillary tubes is less than 50 micrometers. In further embodiments, said electromagnetic radiation is directed in a path less than the width of the inner diameter of said first and second plurality of capillary tubes. It is understood that the effective cross-sectional diameter of the light path depends upon the "tuning" of the laser used, and that persons of skill in the art will know how to adjust the laser to accommodate the above-mentioned constraint. In further embodiments, variations in the capillary alignment in the region of the light-path (the distance out of the array plane, wherein the array plane is defined as a plane congruent with the central axis of the light-path and, ideally, with the central axis of each of the arrayed capillary tubes) are less than 1 micrometer. In further embodiments, variations in the period (the distance between adjacent capillaries in the array plane) are less than 9 micrometers. In other embodiments, the invention relates to a device comprising: i) a transparent material having a first refractive index comprising a) a first plurality of channels filled with a first transparent medium having a second refractive index and b) a second plurality of channels filled with a second medium having a third refractive index; a laser configured to produce a light beam; iii) a reflective surface; and iv) a multichannel photodetector having a plurality of optical fibers; wherein said first and second plurality of channels, at least in the region of the laser's light-path, lie parallel to each other in the array plane, and perpendicular to the central axis of said laser beam. In further embodiments, said reflection surface is configured to reflect scattered light in the direction of said multichannel photodetector. In further embodiments, said reflection surface is a mirror. In further embodiments, said first medium permits fluid to flow therethrough. In further embodiments, said third refractive index is greater than said first refractive index and said third refractive index is greater than said second refractive index. In further embodiments, the absolute value of said third refractive index minus said first refractive index is equal to the absolute value of said second refractive index minus said first refractive index. In further embodiments, said third refractive index is greater than fused silica.

In other embodiments, the invention relates to a linear multi-capillary array comprising: a plurality of active capillaries and, preferably commingled therewith, preferably in one-to-one alternating relation, a plurality of composite optical insertions; wherein said plurality of active capillaries and said composite optical insertions comprise at least two media with different refractive indices, wherein the refractive indices of said active capillaries, said composite insertions and a medium surrounding the linear multi-capillary array's detection zone are selected so that they provide maximum (or at least improved) transmission of the laser beam through the linear multi-capillary array.

In some embodiments, the invention relates to a method of constructing a linear multicapillary array comprising: providing i) a plurality of active capillaries and, preferably commingled therewith, preferably in one-to-one alternating relation, a plurality of composite optical insertions, wherein said plurality of active capillaries and said composite optical insertions comprise at least two media with different refractive indices and ii) a computer; programming said computer to vary the values of parameters associated with formula (1) and formula (2); determining transmittance in relation to said varied values of parameters that provide a desired transmittance; and constructing said linear multicapillary array configured to provide said desired transmittance.

In additional embodiments, the invention relates to a method of sequencing nucleic acid sequences comprising: providing 1) a nucleic acid template having a sequence, 2) all possible nucleotide bases (e.g. fluorescently labeled dNTPs, or ddNTPs) 3) a multichannel capillary electrophoresis system comprising linear arrays disclosed herein and a multichannel photodetection system; performing extension reactions (or polymerase chain reactions) with said nucleic acid sequence under conditions such that a plurality of nucleic acid sequences are formed; detecting said fluorescent labels after performing electrophoresis using the arrays disclosed herein and correlating said detection to the sequence of said nucleic acid sequence.

DETAILED DESCRIPTION OF THE INVENTION

Figure 1:
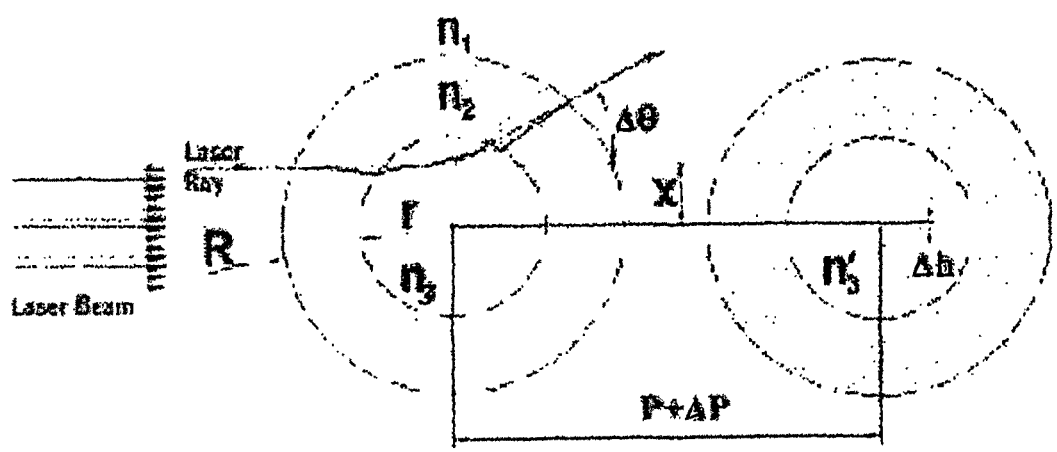
FIG. 1 shows parameters of a capillary array for laser beam tracing.

The invention relates to devices that contain linearly aligned channels having optically transparent substances or materials for focusing light. In some embodiments, the invention relates to improved nucleic acid sequencing methods using devices disclosed herein. In other embodiments, the invention relates to the arrangement of materials in and around capillary tubes with refractive indexes that maximize the number of channels useful for fluorescent detection of compositions after capillary electrophoresis.

The various embodiments of the invention described herein have a variety of applications, including but not limited to, sequencing. Two DNA sequencing methods are in widespread use. These are the method of Sanger, F., Nicken, S. and Coulson, A. R. Proc. Natl. Acad. Sci. U.S.A. 74, 5463 (1977) and the method of Maxam, A. M. and Gilbert, W. Methods in Enzymology 65, 499-599 (1980). The method developed by Sanger is referred to as the dideoxy chain termination method. In the most commonly used variation of this method, a DNA segment is cloned into a single-stranded DNA phage such as M13. These phage DNAs can serve as templates for the primed synthesis of the complementary strand by the Klenow fragment of DNA polymerase I. The primer is either a synthetic oligonucleotide or a restriction fragment isolated from the parental recombinant DNA that hybridizes specifically to a region of the M13 vector near the 3" end of the cloned insert. In each of four sequencing reactions, the primed synthesis is carried out in the presence of enough of the dideoxy analog (ddNTP) of one of the four (A,T,G,C) possible deoxynucleotides (preferably fluorescently labeled) so that the growing chains are randomly terminated by the incorporation of these "dead-end" nucleotides. The relative concentration of dideoxy to deoxy forms is adjusted to give a spread of termination events corresponding to all the possible chain lengths that can be resolved by electrophoresis. The fluorescent tags incorporated in the growing chains are used to determine the pattern of the DNA in each electrophoresis track. The sequence of the deoxynucleotides in the cloned DNA is determined from an examination of the pattern.

The method developed by Maxam and Gilbert uses chemical treatment of purified DNA to generate size-nested sets of DNA fragments analogous to those produced by the Sanger method. Single or double-stranded DNA is labeled at either the 3' or 5' end, can be sequenced by this procedure. In four sets of reactions, cleavage is induced at one or two of the four nucleotide bases by chemical treatment. Cleavage involves a three-stage process: modification of the base, removal of the modified base from its sugar, and strand scission at that sugar. Reaction conditions are adjusted so that the majority of end-labeled fragments generated are in the size range (typically 1 to 400 nucleotides) that can be resolved by electrophoresis. The electrophoresis and pattern analysis are carried out essentially as is done for the Sanger method. (Although the chemical fragmentation necessarily generates two pieces of DNA each time it occurs, only the piece containing the end label is detected.)

As used herein, the term "transparent" means permeable to electromagnetic radiation, preferably, but not limited to, visible light. With regard to materials such as plastic or glass that are transparent, it is not intended that the term be interpreted to require the permeability of all electromagnetic radiation. For example, a material that filters certain visible wavelengths is still considered transparent, as is a material that polarizes or refracts or partially scatters or reflects the radiation.

A "refractive index" is an inherent physically measurable property of a material designated by a number that is the factor by which the phase velocity of electromagnetic radiation is slowed in that material, relative to its velocity in a vacuum. Since the refractive index of a material varies with the frequency (and thus wavelength) of light, sometimes one will specify the corresponding vacuum wavelength at which the refractive index is measured. If not specified the refractive index as provided herein is the refractive index at the Fraunhofer "D" line, the centre of the yellow sodium double emission at 589.29 nm wavelength. A refractometer measures the extent to which light is bent (i.e. refracted) when it moves from air into a sample and is typically used to determine the index of refraction of a liquid sample. Whenever light changes speed as it crosses a boundary from one medium into another its direction of travel also changes, i.e., it is refracted (FIG. 1). (In the special case of the light traveling perpendicular to the boundary there is no change in direction upon entering the new medium.) The relationship between light's speed in the two media, the angles of incidence and refraction and the refractive indexes of the two media is known. Thus, it is not necessary to measure the speed of light in a sample in order to determine its index of refraction. Instead, by measuring the angle of refraction, and knowing the index of refraction of the layer that is in contact with the sample, it is possible to determine the refractive index of the sample. The refractive index of certain media may be different depending on the polarization and direction of propagation of the light through the medium (in anisotropic media). Here, it is assumed that the refractive index is always correlated to the direction in which a laser beam is propagating.

As used herein, a "laser" means a combination of parts and/or devices that amplify light by stimulated emission of radiation. In a typical laser, the lasing medium is "pumped" to get the atoms, preferably of the same element, into an excited state. Typically, very intense flashes of light or electrical discharges pump the lasing medium and create a large collection of excited-state atoms (atoms with higher-energy electrons). Once the lasing medium is pumped, it contains a collection of atoms with some electrons sitting in excited levels that produce photons. The photon emitted has a very specific wavelength. Stimulated emission occurs when a photon (possessing a certain energy and phase) encounters another atom that has an electron in the same excited state causing an emission. In many lasers, photons with a very specific wavelength and phase reflect off mirrors to travel back and forth through the lasing medium. In the process, they stimulate other electrons to make the downward energy jump and can cause the emission of more photons of the same wavelength and phase. Cascade effect occurs, and soon propagates many photons of the same wavelength and phase. The mirror at one end of the laser reflects some light and lets some light through. The light that makes it through is the laser beam. It is understood that the laser is pointed in the direction that this light travels.

As used herein, a "channel" means a volume bound in a solid material. The channel is often used to hold a liquid or solid of a desired refractive index. It is not intended that the term be limited to those volumes that allow a consistent flow of a liquid, i.e. the channel may be an entirely enclosed volume. It is not intended that the channels be of any specific shape. However, in preferred embodiments, the channels are shaped as cylinders. In an even more preferred embodiment, the channels are capillary tubes. Two channels are aligned in parallel when lines extended along the bore or the central axis of each channel first intersect at infinity. A channel lies in an array plane when the bore or central axis of the channel lies in a plane that is congruent with the central axis of the light-path of a laser of the invention. A channel is perpendicular to the light-path of a laser of the invention when the channel's bore or central axis is perpendicular to the central axis of the light-path. It is understood that for practical purposes the channels are situated with certain locational deviations such that the channels are "substantially" parallel, as no perfectly parallel configuration can be actually produced. Similar practicalities obtain when describing a channel as being perpendicular to the light-path of a laser, or as lying in an array plane. A linear multicapillary array comprises a plurality of channels aligned in parallel, each lying in an array plane perpendicular to the central axis of the light-path of a laser of the invention.

It is also understood that it is not necessary for the entire channel to conform to the foregoing geometrical definition. For example, flexible tubes can be used as channels and, in some embodiments, portions of the flexible tubes may overlap or bend in any direction. The geometrical constraints outlined above need apply only to the region of the tube at or near the point of intersection with the light-path of the laser beam.

Capillary action or capillarity or capillary motion occurs when the adhesive intermolecular forces between a liquid and a solid are stronger than the cohesive intermolecular forces within the liquid. For example, a narrow tube with a large surface area draws a liquid upwards against the force of gravity. This narrow tube is typically referred to as a capillary tube.

Electrophoresis is the differential movement or migration of ions by attraction or repulsion in an electric field. Typically, a positive (anode) and a negative (cathode) electrode are placed in a solution containing ions. Then, when a voltage is applied across the electrodes, solute ions of different charge, i.e., anions (negative) and cations (positive), will move through the solution towards the electrode of opposite charge. For example, nucleotide sequences are connected by phosphate ions, which will migrate by electrophoresis.

Capillary electrophoresis is the technique of performing electrophoresis in a channel that provides capillary action, e.g., a tube capable of drawing a liquid upwards against the force of gravity. Typically, the ends of a capillary tube are placed in separate buffer reservoirs, each containing an electrode connected to a voltage power supply. A sample is injected onto the capillary by temporarily replacing one of the buffer reservoirs (normally at the anode) with a sample reservoir and applying either an electric potential or external pressure for a few seconds. After replacing the buffer reservoir, an electric potential is applied across the capillary and the separation is performed. Optical (e.g., UV-visible or fluorometric) detection (photodetector) of separated analytes may be achieved directly through the capillary wall (channel) near the opposite end (preferably near the cathode). A multichannel photodetector or multipixel photodetector is a device that detects the optical properties of two or more channels As used herein, an "active capillary" refers to a capillary used in capillary electrophoresis in which a sample is intended to be separated and is subject to optical detection.

As used herein, a "composite optical insertion" refers to a material or mixture of materials that have desired optical properties, preferably a desired refractive index.

As used herein, a "medium" refers to a substance or consistent mixture of substances that has a constant physical characteristic, such as a desired refractive index.

As used herein, "transmission" means the fraction of radiant energy that passes through a substance. In optics, a transmission coefficient is a measure of how much of an electromagnetic wave (e.g., light) passes through a surface or an optical element. Transmission coefficients can be calculated for either the amplitude or the intensity of the wave. Either is calculated by taking the ratio of the value after the wave has passed the surface or element to the value before.

Fused quartz is a noncrystalline form of silicon dioxide ($SiO_2$), which is also called silica. The crystalline form of this material is also named quartz; however, as used herein, the term quartz means fused quartz unless expressly referring to the crystalline form.

An optical fiber or fibre is a thin, transparent fiber, usually made of glass or plastic, for transmitting light. Such fibers are often called waveguides. Light collection and detection systems utilize the photoelectronic effect by transmitting light by optical fiber to photodiodes. The photoelectric effect is the emission of electrons from matter upon the absorption of electromagnetic radiation. Upon exposing a metallic surface to electromagnetic radiation that is herein the threshold frequency (which is specific to the type of surface and material), the photons are absorbed and current is produced. A photodiode is a semiconductor diode that functions as a photodetector. Photodiodes are packaged with either a window or optical fibre connection As used herein, "high aperture projection optics" refers to an optical device that permits an image to be projected at high magnification and resolution. In particular, high aperture projection optics permits the fluorescent emissions from the ends of any two adjacent capillary tubes to be detected as emissions from two distinct sources ("resolution") even when the total linear array of tubes is long (i.e., the device has a large "collection angle.").

As used herein, a "cover" means something that covers or is laid, placed, or spread over or upon something else.

As used herein, a "chip" means a single piece of material, e.g., glass or silicon.

As used herein, a "mirror" means a reflecting surface. Usually mirrors are made of plate glass, one side of which is coated with metal or some special preparation to serve as a reflecting surface. The junction of this reflecting surface and the plate glass is called the mirror line. Highly polished metal and other materials serve also as mirrors. Three common types of mirror are the plane mirror, which has a flat, or plane, surface; the convex mirror; and the concave mirror. Convex and concave mirrors are known collectively as spherical mirrors, since their curved reflecting surfaces are usually part of the surface of a sphere. The concave type is one in which the midpoint or vertex of the reflecting surface is farther away from the object than are the edges. The center of the imaginary sphere of which it is a part is called the center of curvature and each point of the mirror surface is, therefore, equidistant from this point. A line extending through the center of curvature and the vertex of the mirror is the principal axis, and rays parallel to it are all reflected in such a way that they meet at a point on it lying halfway between the center of curvature and the vertex. This point is called the principal focus.

A dielectric mirror is a special kind of a mirror, made of a substrate, e.g., glass or some other optical material, on which one or more thin layers of dielectric material are deposited, to form an optical coating. By careful choice of the type and thickness of the dielectric layers, the range of wavelengths and amount of light reflected from the mirror can be specified.

As used herein, a "compartment" means a structure such as a box or bucket that is capable of confining a material. It is not intended to be limited to an entirely enclosed structure. In some embodiments, materials may be added or removed from the structure.

As used herein, a "medium" means any of a variety of solids or liquids.

As used herein a "porous material" means a variety of materials that allow the passage of a liquid through the material.

In linear multicapillary arrays (LMCAs) the throughput of DNA sequencing machines can be significantly increased by increasing the number of simultaneously operated capillary lanes. Array illumination systems preferably are: (i) uniformity of the array irradiation and (ii) delivery of a certain illumination power to each individual capillary of the array.

Obtaining a uniform illumination of LMCA with a large number of capillaries requires a relatively high refractive index (n) of the separation polymer (n close to 1.4000). Media with lower refractive indices, such as water or low viscosity polymers, cannot be used, as they lead to beam divergence.

U.S. Pat. No. 5,938,908 discloses a cylindrical glass rod made of quartz (fused quartz refractive index of 1.46) arranged between quartz capillaries to condense the laser light. This approach introduces additional attenuation of the laser beam due to the increase in the reflection loss on the interfaces between the lenses and the surrounding medium. This approach introduces additional attenuation of the laser beam due to the increase in the reflection loss on the interfaces between the lenses and the surrounding medium. Thus, ultimately LMCAs with rod inserts do not allow any actual increase in the number of capillaries in the array when compared to simple LMCAs. U.S. Pat. No. 5,938,908 also discloses that quartz capillaries filled with a liquid with a refractive index close to that of quartz glass may be used in place of the quartz rods, e.g., the inside of the capillaries may be filled with formamide (refractive index: 1.45). However such an arrangement does not improve fluorescence resolution by providing uniformity of the array irradiation and delivery of a miniumum illumination power to each individual capillary of the array for large numbers of working capillaries.

Herein the Applicant discloses the use of composite insertions in conjunction with a surrounding refractive index medium that matches the refractive index of capillary walls. Computer simulations and experimental studies show that for the dual-side illumination scheme, the approach allows uniform illumination of LMCA with as many as 550 working capillaries.

The Applicant does not intend to be limited any particular mechanism; however, it is believe that when a laser beam traverses the length of a multicapillary array, it passes a number of interfaces of media with different refractive indices. Because of reflection and refraction of the beam on these interfaces the beam power decreases along the capillary array. To calculate the beam intensity profile along the capillary array, a software tool was developed based on a model of beam propagation (FIG. 1). The medium around the capillaries has refractive index $n_1$. The array is formed from capillaries of inner radius r, outer radius R, positioned with period P. The capillary wall has refractive index $n_2$, the medium inside the capillary has refractive index $n_3$, and the medium in the composite insertion has refractive index $n'_3$. The laser beam of diameter D is treated as a set of discrete rays. Distance x from the capillary center to the incident point of each ray varies from zero to D/2. After passing through a capillary, each ray has a difference in angle $\Delta\theta$ with respect to the direction of the incidence. This change of angle is due to the beam passing multiple interfaces (capillary walls) with different refractive indices, and is given by the following expression:

$$\Delta\theta = 2\left[-\sin^{-1}\left(\frac{x}{R}\right) + \sin^{-1}\left(\frac{n_1 x}{n_2 R}\right) - \sin^{-1}\left(\frac{n_1 x}{n_2 r}\right) + +\sin^{-1}\left(\frac{n_1 x}{n_3 r}\right)\right] \quad (1)$$

To analyze stability of the array transmittance with respect to small fluctuations of the system's parameter values that are consistent with imperfections introduced during array manufacturing, a variation, $\Delta P$, was introduced in the array period and a deviation, $\Delta h$, was applied to the vertical alignment of the capillary centers. An in-house software package was developed consisting of two pieces of software that were used to simulate light propagation through the LMCA. The first software program simulates light propagation through a set of optical objects using ray tracing and geometric optics. As specified above, it accounts for the changes in a light ray as it passes through different media with varying refraction indices. The second piece of software is used to automatically generate the set of primitive optical objects to be processed. This allows us to analyze capillary configurations with various numbers of capillaries, distance between them, precision of capillary placement, various refraction indices, and other LMCA parameters. To compute the fraction of light T that is transmitted through the boundary of two media with refractive indices $n_1$ and $n_2$ we used the following formulas:

$$T = 1 - \frac{\left(\frac{n_1\cos\theta_i - n_2\cos\theta_t}{n_1\cos\theta_i + n_2\cos\theta_t}\right)^2 + \left(\frac{n_2\cos\theta_i - n_1\cos\theta_t}{n_2\cos\theta_i + n_i\cos\theta_t}\right)^2}{2} \quad (2)$$

where $\theta_t=\arcsin[n_1 \sin(\theta_1)/n_2]$.

Using this software package, a computer carried out simulation and optimization of the light transmittance of multicapillary arrays and optimized the array design in order to maximize the number of capillaries which would allow a uniform dual side illumination, while determining the robustness of the transmittance with respect to the array's manufacturing imperfections.

Figure 7A:
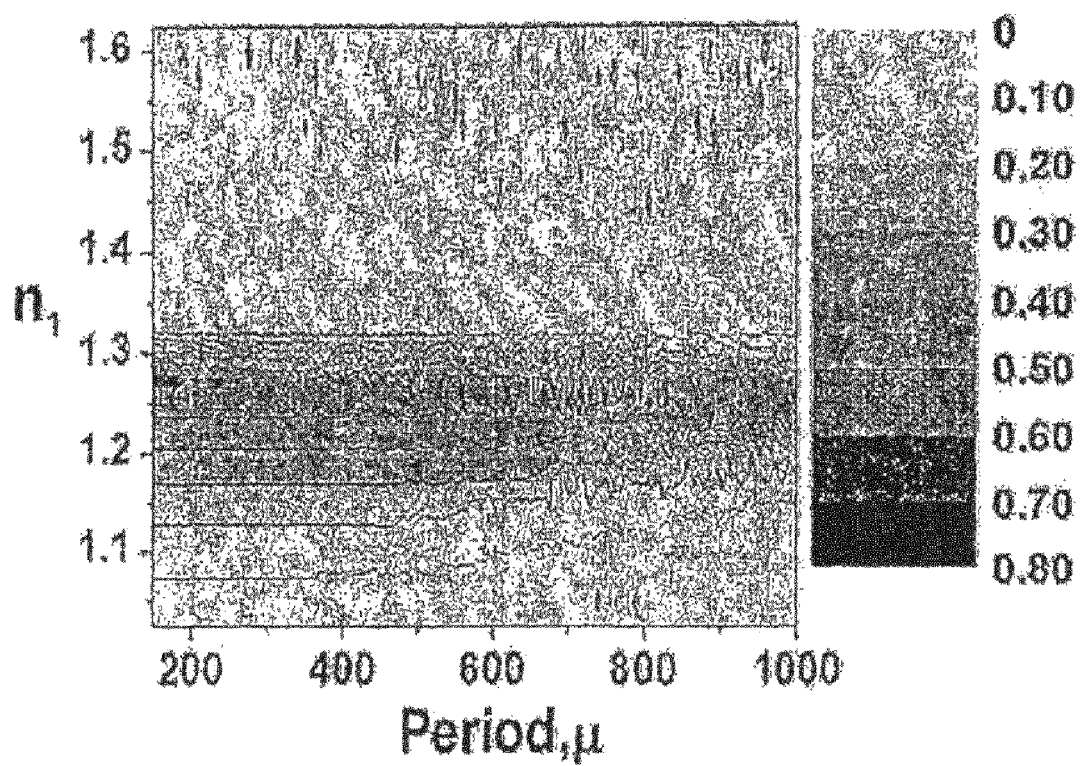
FIGS. 7A and 7B show the transmittance of 48-capillary arrays. (A) Array without insertions, $n_3=1.4000$; (B) array with composite insertions, $n_1=1.4614$.
Figure 7B:
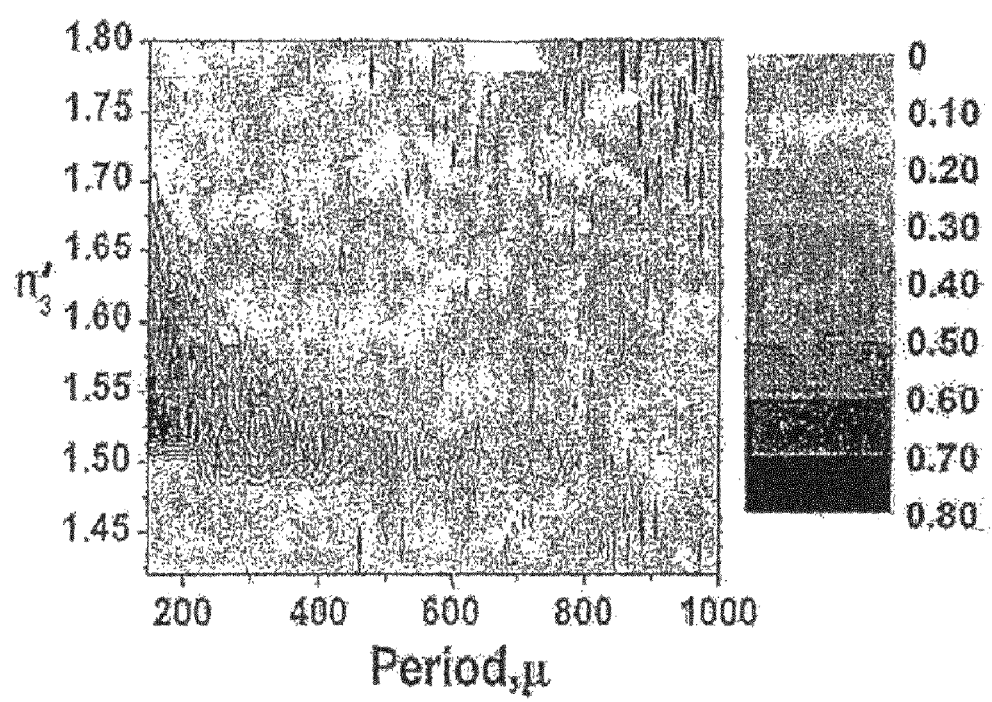

Computer simulations of the light propagation were carried out for a wide variety of capillary arrays. Note that practical array fabrication with capillary alignment is preferred if the outer diameters of active capillaries and insertions are equal. In the following embodiment, inserts have a single inner diameter because both active capillaries and insertions are preferred to be fabricated in the same capillary pulling process and Design optimization was done by varying the refractive indices of participating media. In our simulations inner capillary diameter of 50 mm were chosen, a preferred choice for DNA sequencing performance. Because, in some embodiments, the proposed design is intended for DNA sequencing, we chose the refractive index of active capillaries $n_3$=1.4000 which corresponds to the refractive index of the commercial separation polymer POP-7 from ABI. Results obtained for capillary arrays formed from fused-silica capillaries with inner diameter 50 mm and outer diameter 150 mm are presented, since such capillary parameter values are used in the experimental studies. FIG. 7 shows the transmittance coefficient for 48-capillary arrays as a function of the refractive index of the surrounding medium $n_1$, the array period, and the refractive index of the composite insertions $n'_3$. The simulation results show that for arrays without insertions (conventional structure) the highest array transmittance (~0.7) is obtained for values of $n_1$ below 1.3000. Although it is possible to find exotic liquids with refractive indices lower than 1.3000 (for example 3M™ Fluorinert™ Electronic Liquid FC-72 by 3M, USA has n=1.2510), they usually have some undesirable properties such as a low boiling point, fluorescence, and others, which limit their use for CE. The liquid used in commercially available capillary arrays from ABI has refractive index 1.2925 (such as Cargille Labs Code 433 fluid with n=1.2930-1.3025) for which the array transmittance is about 0.5. For the array with composite insertions, the highest transmittance of ~0.7 is obtained when $n_2$-$n_3$=negative $n'_3$-$n_2$.

However, in contrast to conventional arrays, the array with composite insertions can be built using media with refractive indices higher than 1.3300. Such materials are widely available both as liquid or solid UV curable compounds. As can be seen, the transmittance for the array without insertion shows low sensitivity to the array period (FIG. 7). In contrast, in the array with composite insertions the transmittance decreases very rapidly with increase in the array period. This can be explained by the fact that in conventional arrays due to a specific combination of refractive indices ($n_2$ greater than $n_3$ greater than $n_1$) each individual capillary is equivalent to a pair of focusing and defocusing interfaces. Thus, the deviation of the laser beam from its original direction is minimal and is practically independent of the distance between capillaries.

Figure 8:
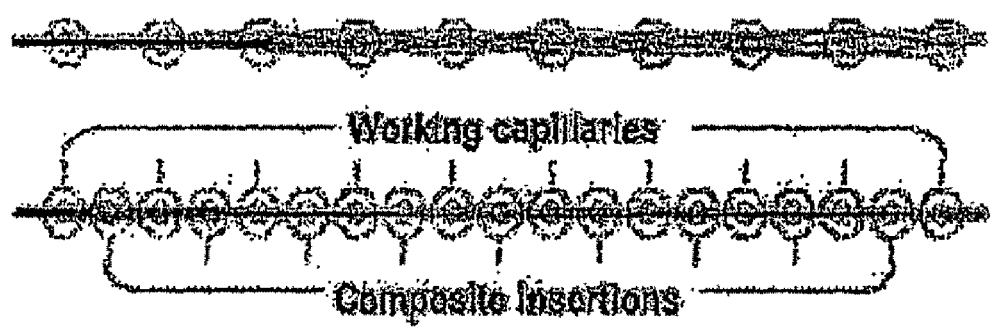
FIG. 8 shows ray tracing simulations. Unsuccessful beam propagation in the array without insertions (upper array; $n_1=1.2925$, $n_2=1.4614$, $n_3$ 32 1.3830) and successful propagation of the laser beam in the array with insertions (lower array; $n_1=1.2925$, $n_2=1.4614$, $n_3=1.3830$, $n'_3=1.5250$).
Figure 9A:
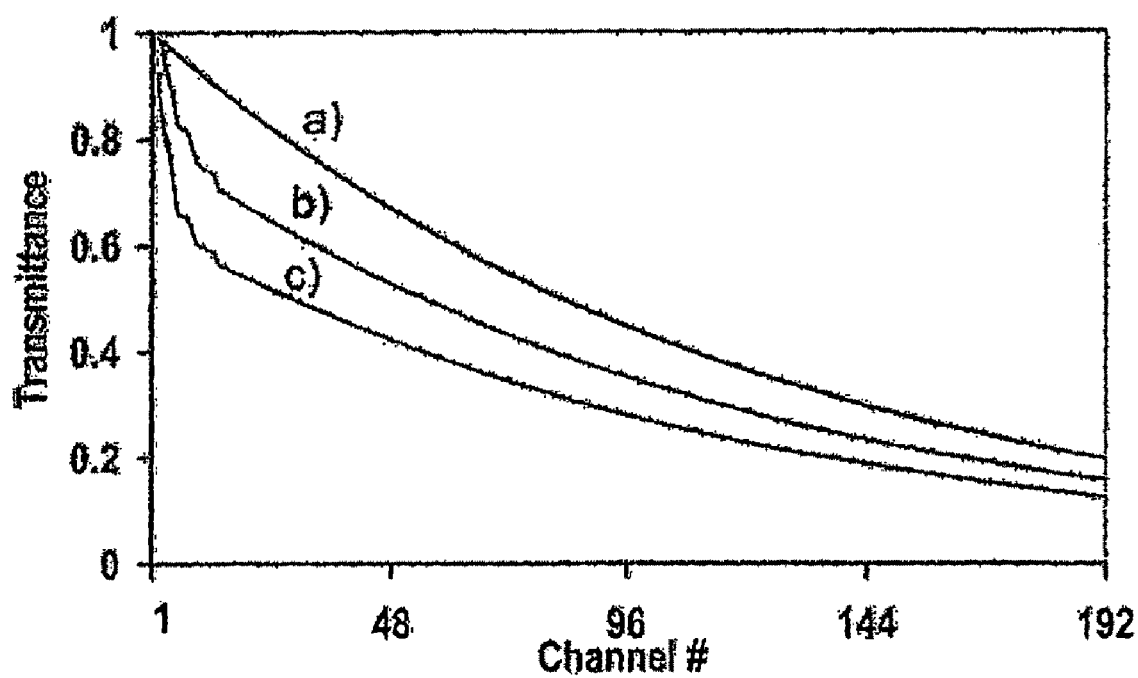
FIGS. 9A and 9B show transmittance vs. the capillary number for optimum parameter values calculated for three diameters D of the laser beam: (a) D=30 mm; (b) D=40 mm; (c) D=50 mm. Array without insertions (top): $n_1=1.2925$, $n_2=1.4614$, $n_3=1.4000$; array with insertions (bottom) $n_1=n_2=1.4614$, $n_3=1.4000$, $n'_3=1.5250$.
Figure 9B:
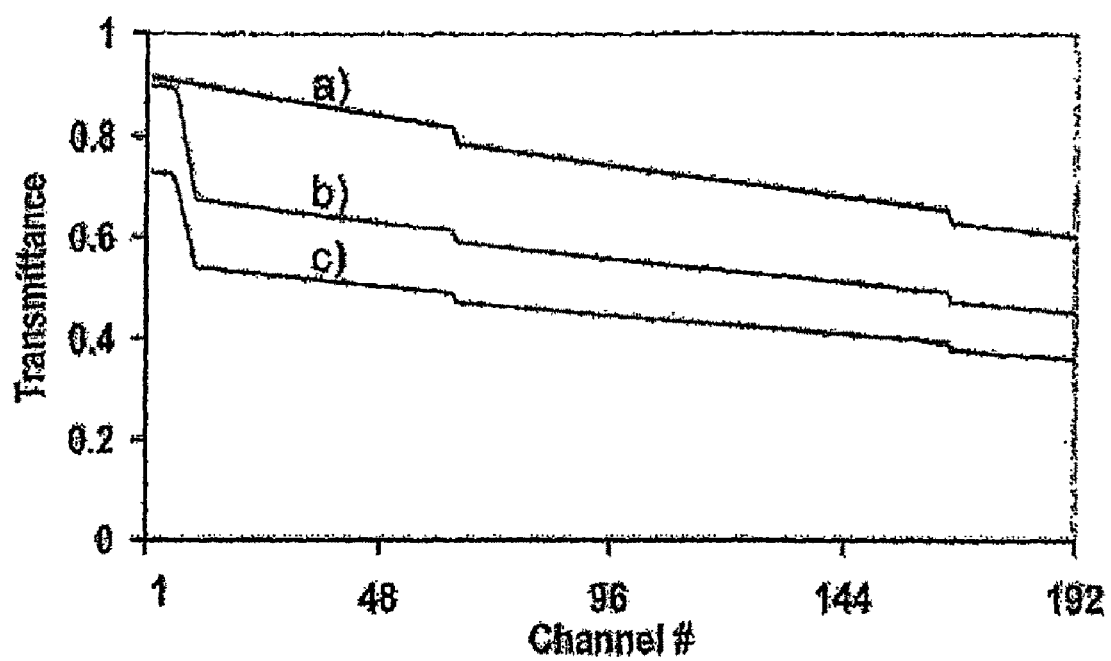
Figure 10A:
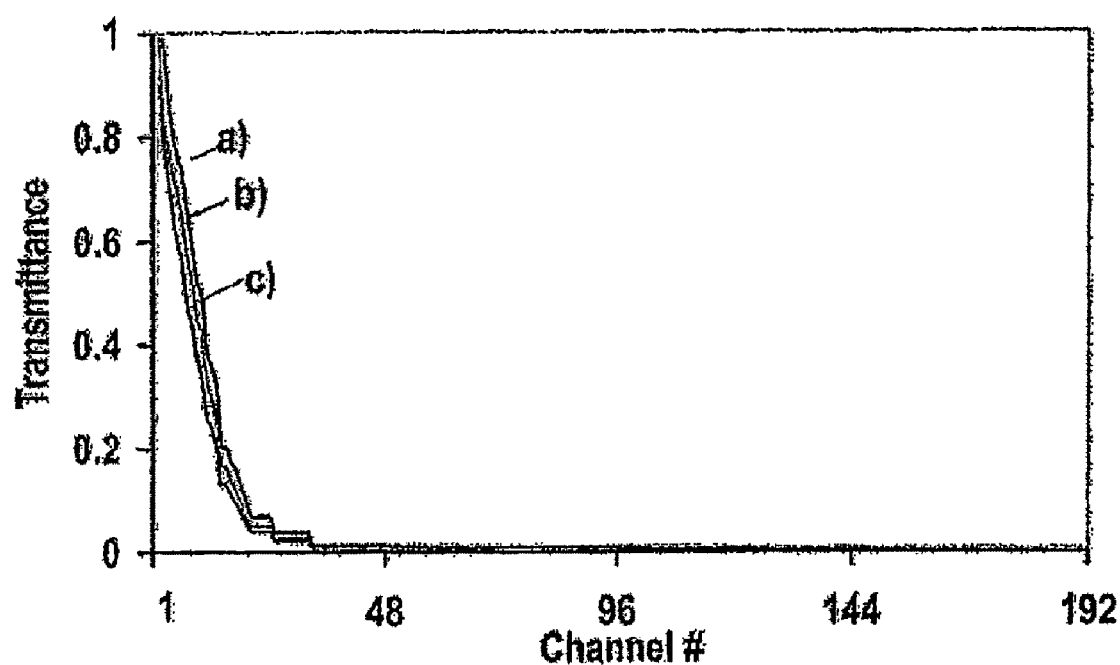
FIGS. 10A and 10B show transmittance vs. the capillary number for a nonoptimum set of parameter values calculated for three diameters D of the laser beam: (a) D=30 mm; (b) D=40 mm; (c) D=50 mm, Array without insertions (top): $n_1=1.2925$, $n_2=1.4614$, $n_3=1.3830$; array with composite insertions (bottom) $n_1=n_2=1.4614$, $n_3=1.3830$, $n'_3=1.5250$.
Figure 10B:
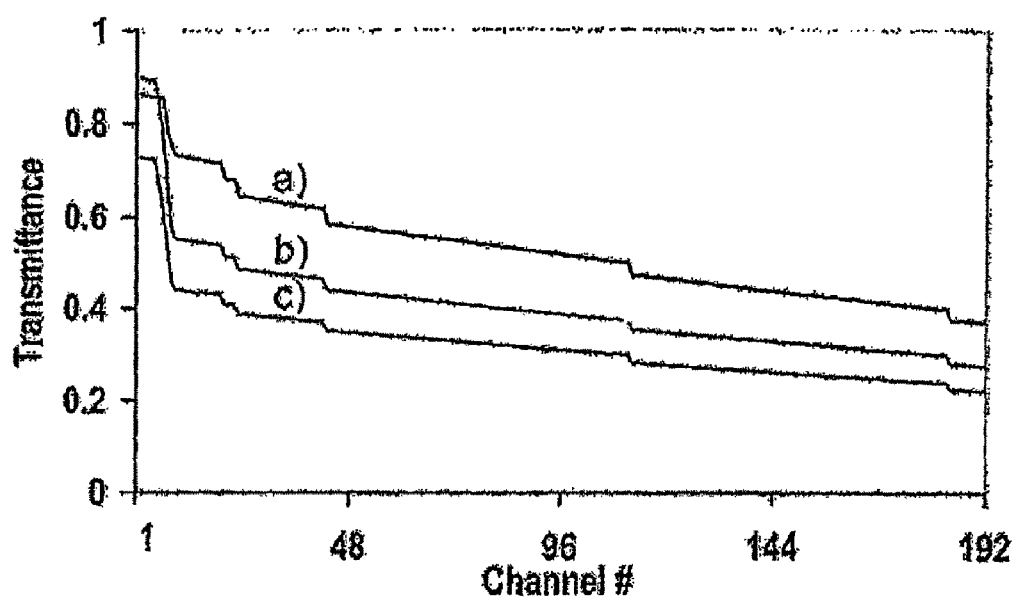

In the structure with insertions there is no optical interface between the surrounding medium and capillary walls ($n_1$=n2). Therefore, working capillaries defocus the laser beam since $n_3$ is smaller than $n_2$. To compensate for this defocusing, the composite insertions which have $n'_3$ greater than $n_2$ should be placed close enough to the working capillaries. Otherwise, some portion of the beam will be lost (see examples of successful and unsuccessful beam propagation in FIG. 8). In order to determine the maximum number of capillary lanes in LMCAs, the distribution of the light transmittance across capillary arrays was calculated (FIG. 9). For arrays without insertions parameter values were used that corresponded to commercially available arrays from ABI. For array with composite insertions the following parameter values were selected: array period −300 mm (equal to double the outer diameter); refractive index of the capillary walls $n_2$=1.4614; refractive index of the separation gel $n_3$=1.4000 and the refractive index of insertions $n'_3$=1.5250. In the conventional structure, the decay of the laser beam along the array was found to be much faster than in the structure with composite insertions. However, for 48-capillary arrays (the configuration we used in our experiments), the array transmittance was practically the same for both arrays with and without insertions (see FIG. 9). In order to better demonstrate advantages of the proposed array configuration, we carried out the array simulation with refractive index of the separation polymer $n_3$=1.3830. As can be seen in FIG. 10, the array with composite insertions is much more stable with respect to variations of the refractive index of the polymer (see FIG. 10). In our further studies we chose 50% transmittance in the middle of the capillary array as an acceptable threshold transmittance of the array. In this case the dual-side illumination scheme provides practically uniform irradiation of the entire array. Based on this criterion and the above simulation results, we conclude that conventional arrays may consist of ~150 capillaries for the 30 mm laser beam, while for the newly proposed array with composite insertions even 394 capillaries are far from the transmittance threshold. Simulation for 500-capillary array showed that the threshold value of 50% beam transmittance is reached at 275 capillaries in row. Therefore, in dual-side illumination scheme linear capillary arrays comprising of as many as 550 capillaries can be used.

Advantages of the newly proposed structure become even more pronounced for CE systems in which the refractive index of working media is close to 1.3300. As we can see in FIG. 11, for capillary arrays with conventional structure (air and ABI) transmittance becomes unacceptable at the 20th capillary while the structure with insertions continues to guide the beam.

Figure 11:
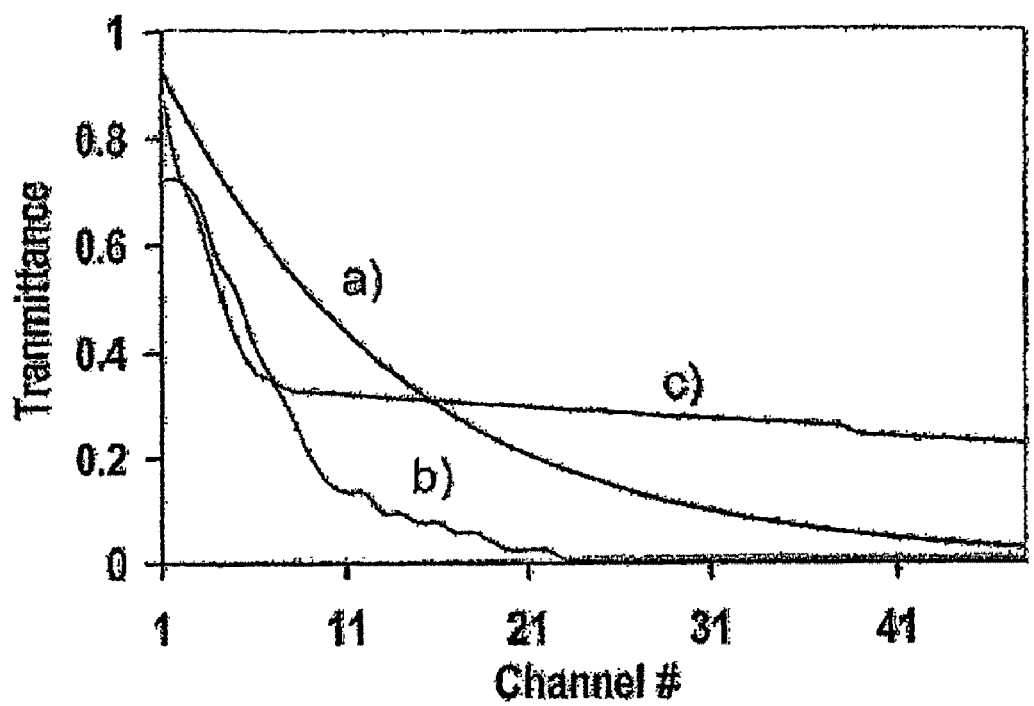
FIG. 11 shows transmittance vs. the capillary number for working media with $n_3=1.3300$. (a) $n_1=1.0000$ (air); (b) $n_1=1.2925$ (used in ABI arrays); (c) for structure with insertions having $n_1=n_2$ and $n'_3=1.5900$.

All transmittance curves shown in FIGS. 9-11 exhibit step-like patterns. This is because in our computer simulation the laser beam was represented by a set of 60 discrete rays. Steps in the transmittance characteristics correspond to moments when two peripheral rays diverge so that they are not further guided by the array, while the gradual decay of the transmission coefficient is due to the reflection loss of light intensity.

Since fabrication of real capillary arrays can only be done with a certain degree of accuracy, we carried out a comprehensive stability analysis of the newly proposed structure in the presence of small fluctuations of the array's parameter values introduced by manufacturing. We took into account the following sources of fabrication inaccuracy:

(1) Tolerance ΔP of the array period caused by a finite precision of the capillary fixture.

(2) Shift of vertical position of capillary centers Δh due to finite precision of capillaries' fixture and slight variations in the outer diameter of capillaries.

Figure 12:
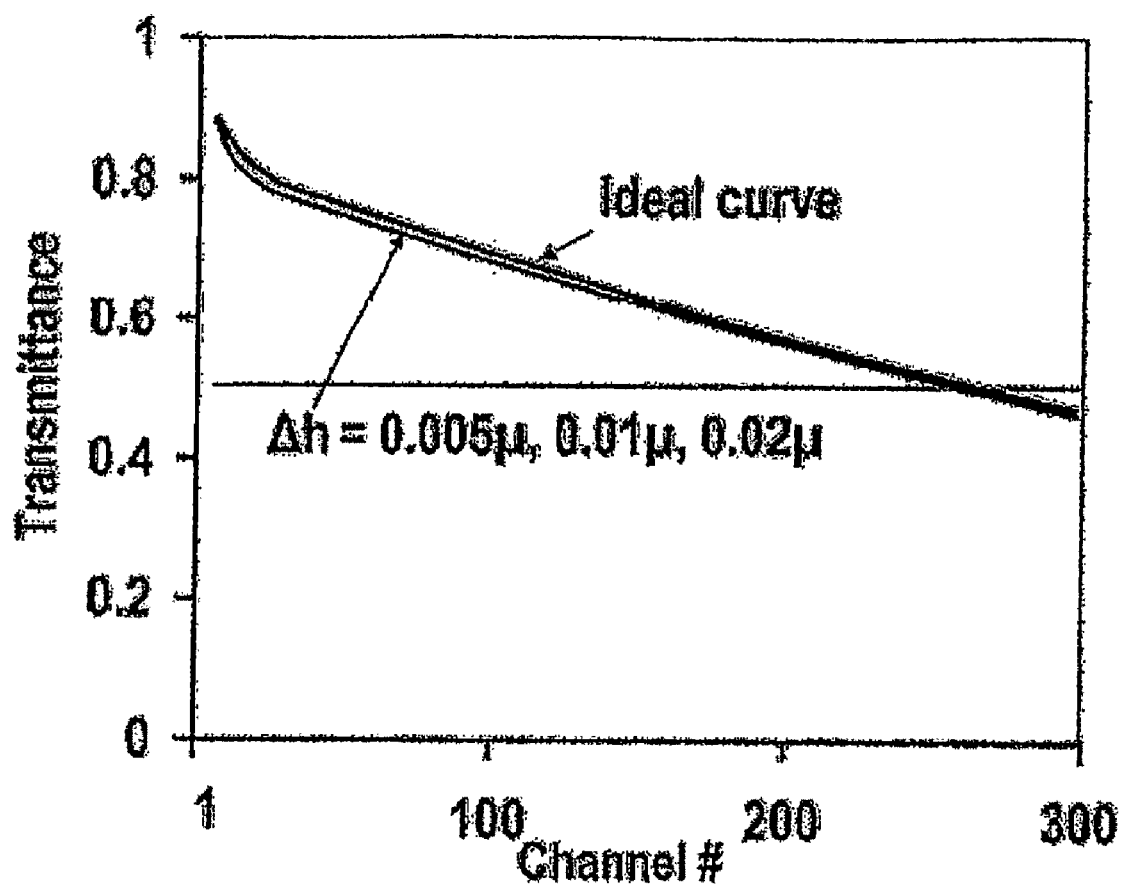
FIG. 12 shows transmittance profile in the array with composite insertions for smooth change in vertical alignment of capillary centers (D=30 mm).

At first, simulations for a smooth increase in the capillary's vertical alignment Δh caused by a smooth change of the capillary diameter were performed within one commercial capillary lot (FIG. 12). Our simulations showed that smooth change in position of capillary centers practically did not change light guiding properties of structures with insertions. In an array with 50 cm capillary length, the biggest difference of 0.02 mm between neighbor elements of the array corresponds to 11 mm between the first and the last elements of the 550-capillary array (note that this is within the fabrication tolerance for commercial fused-silica capillaries (e.g., Polymicro Technologies, Ariz., USA). In the next simulation, imprecise placement of capillaries was simulated along the plane of the array, by introducing fluctuations of the array period ΔP according to normal distribution with a specified variance:

$$f(\Delta P) = \frac{1}{\sqrt{2\pi}\,\sigma_P} \exp\left(-\frac{(\Delta P - P_0)^2}{2\sigma_P^2}\right) \quad (3)$$

Figure 13:
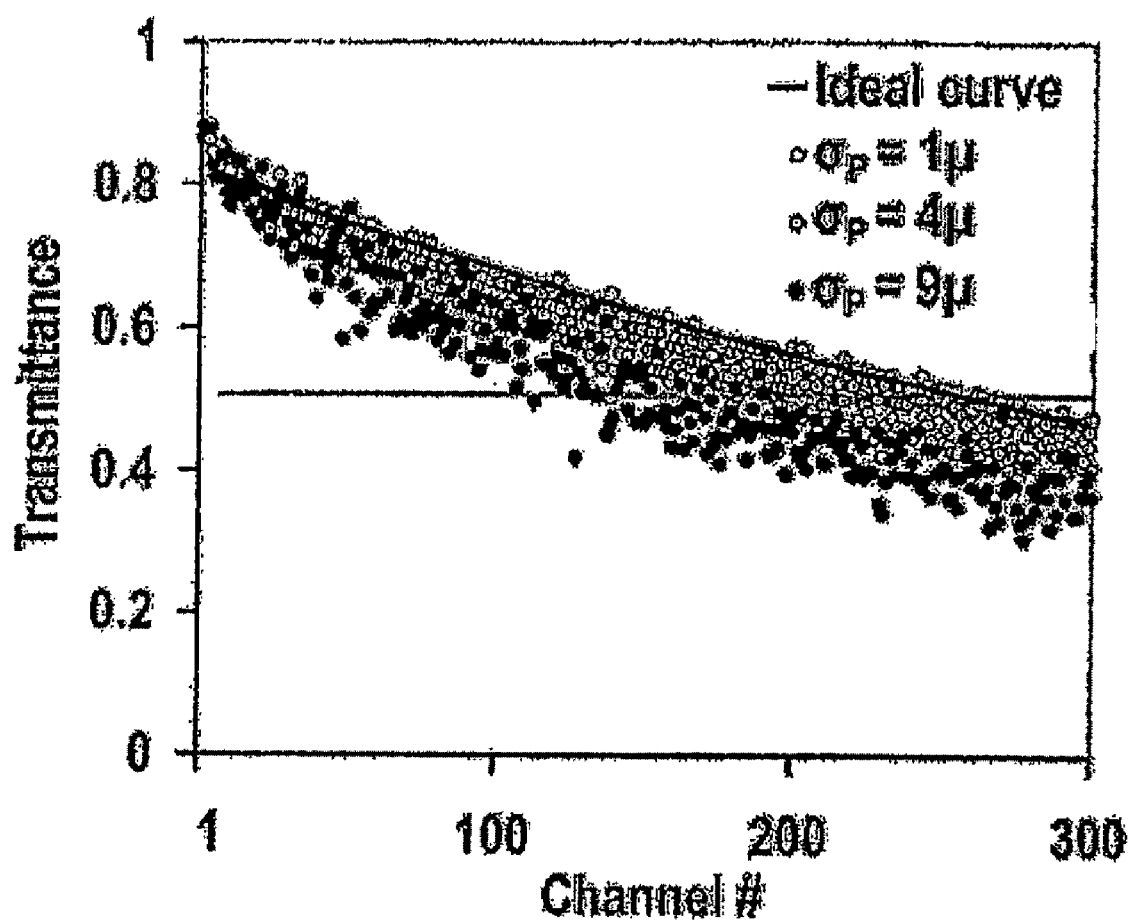
FIG. 13 shows transmittance profile in the presence of small fluctuations in the array's period (D=30 mm).
Figure 14:
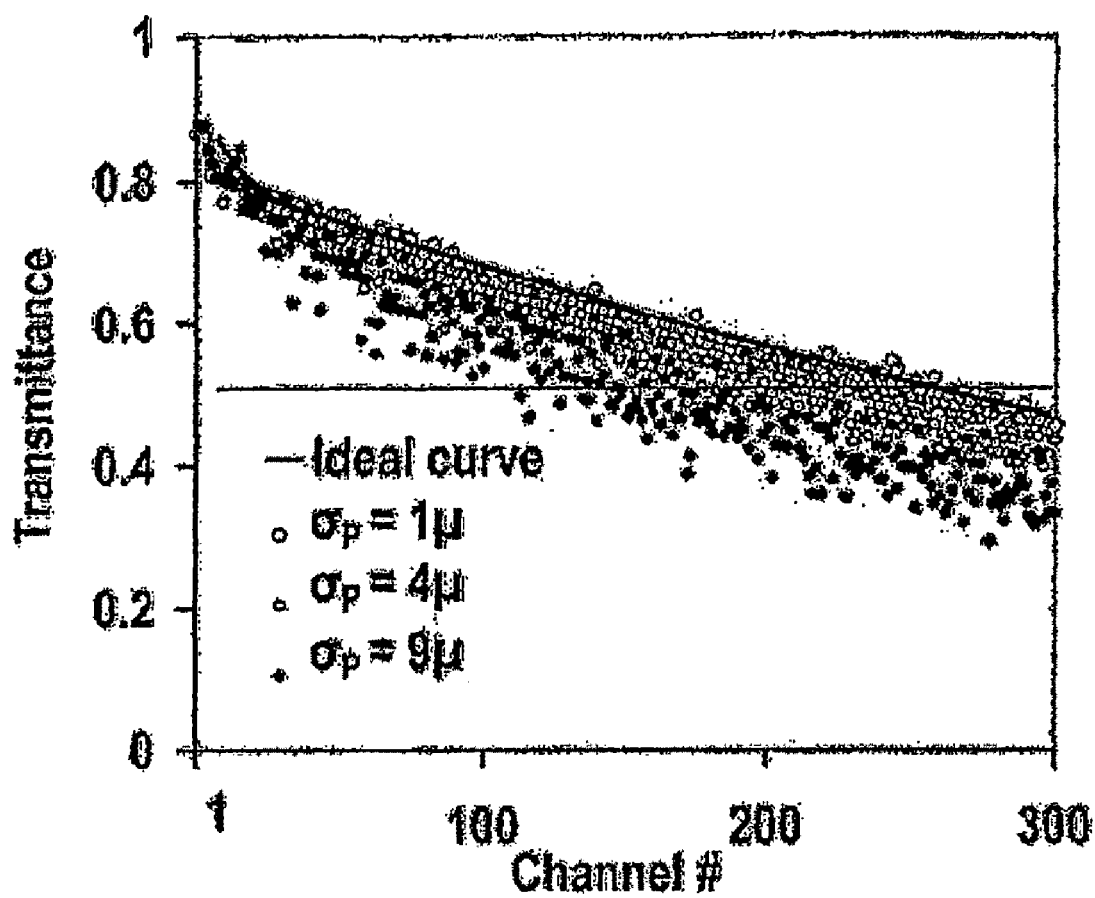
FIG. 14 shows transmittance profile in the presence of fluctuations of the array's period and smooth change in vertical alignment of capillary centers Δh=0.02, D=30 mm).

For values of SDs $\sigma_p$ less than or equal to 1 mm changes in the array transmittance are slight compared to the ideal case. Larger values of $\sigma_p$ cause a noticeable degradation of the array transmittance. Such a behavior is understandable from analysis of FIG. 7B, which shows a strong dependence of the array transmittance on the array period. FIG. 14 presents the laser beam transmittance for an array with small fluctuations of the period and smooth change of the vertical alignment of capillary centers. The obtained results are similar to that shown in FIG. 13 since a smooth change of the capillaries' vertical position practically does not influence the array's light guiding properties.

Figure 15:
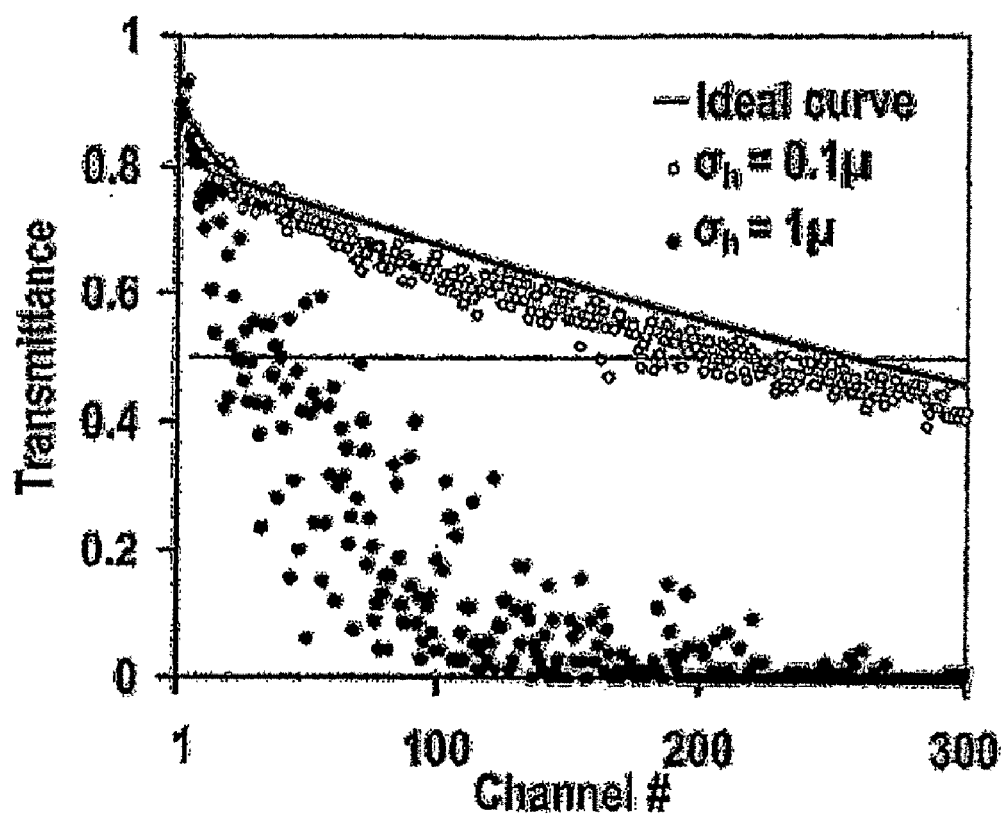
FIG. 15 shows transmittance profile for array with fluctuations in vertical alignment of capillary centers (D=30 mm).

FIG. 15 shows simulation results obtained for an array with small random fluctuations of the vertical position of the capillary according to the normal distribution. As follows from FIG. 15, the preservation of the array light-guiding properties requires that fluctuations in vertical capillary alignment would be less than ±0.1 μm. Increase in the fluctuation amplitude causes a degradation of the array's light-guiding properties. Thus, the performed simulations show that it is preferred to avoid random fluctuations in capillary outer diameters. This can be done if we form the arrays from capillaries cut one by one from me same lot or capillary tubing, since in this case position of capillary centers will smoothly "drift" along the vertical axis of the array. Performed simulations show that newly proposed capillary arrays with composite insertions are sensitive to variations in their period and vertical capillary alignment. The required tolerances can be achieved using silicon v-grove as a fixture for capillaries alignment.

Two series of experiments have been performed. In each series, illumination efficiency for 48-capillary arrays of two configurations was compared: conventional (with working capillaries only) and proposed (with composite insertions). In all experiments as a source of fluorescence POP-7 gel was used with $10^{-6}$ M TAMRA. The two series differed in refractive indices for liquids used in working (active) capillaries ($n_3$ above). In the first series of experiments we measured transmittance of 48-capillary arrays having optimum combination of refractive indices predicted by our calculations. In this second series, working capillaries of all arrays were filled with a mixture of 99% POP-7 and 1% of $10^{-4}$ M solution of TAMRA in deionized water (to the fmal dye concentration of $10^{-6}$ M) having refractive index of active capillaries $n_{3optimal}=1.3990$. In the second series the active capillaries of all arrays were filled with a mixture of 90% POP-7 and 10% of $10^{-5}$ M solution of TAMRA (to the final dye concentration of $10^{-6}$ M) The mixture had the refractive index of active capillaries $n_{3nonoptimal}=1.3830$. This series aimed at the demonstration of the influence of the refractive index change on the array's transmittance. In both series the composite insertions were formed by filling even-numbered capillaries of the 96-capillary array with refractive index liquid having $n'_3=1.5250$, and the original matching liquid in detection cell (FIG. 2) was replaced with fused-silica matching liquid with refractive index $n_1$ new=1.4614.

TABLE 1

Refractive indices

| | |
|---|---|
| Capillary's wall (fused-silica glass) | $n_2$ = 1.4614 at 530 nm |
| Original matching liquid for ABI detection cell | $n_1$ = 1.2925 |
| Matching liquid for detection cell of capillary array with insertions | $n_{1new}$ = 1.4614 at 530 nm |
| Index of liquid inside composite insertions | $n'_3$ = 1.5250 at 530 nm |
| POP-7 with $10^{-6}$ M TAMRA dye (99% POP-7 + 1% TAMRA $10^{-4}$ in $H_2O$) - optimal configuration | $n_{3optimal}$ = 1.3990 |
| POP-7 with $10^{-6}$ M TAMRA dye (90% POP-7 + 10% TAMRA $10^{-5}$ in $H_2O$) - non-optimal configuration | $n_{3nonoptimal}$ = 1.3830 |

Figure 16:
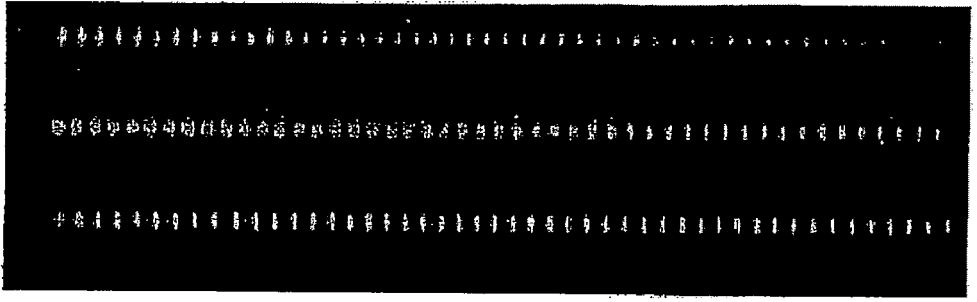
FIG. 16A shows photographs of the fluorescence excited in a forty-eight capillary array, no insertions, $n_3=1.383$ (non-optimal).
FIG. 16B shows photographs of the fluorescence excited in a forty-eight capillary array, no insertions, $n_3=1.4$ (optimal).
FIG. 16C shows photographs of the fluorescence excited in a forty-eight capillary array, with insertions, $n_3=1.4$ (optimal).
Figure 17:
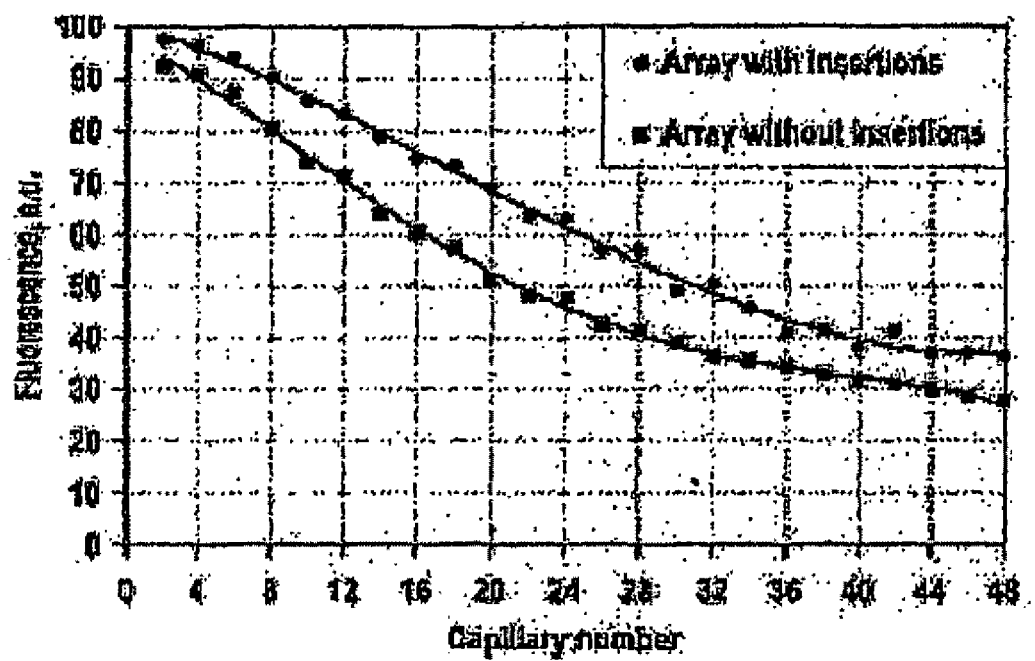
FIG. 17 shows the distribution of fluorescence intensity in a capillary array for an optimum combination of refractive indices (array without insertions: $n_1=1.2925$, $n_2=1.4614$, $n_3=1.4000$; array with insertions: $n_1=1.4614$, $n_2=1.4614$, $n_3=1,400$, $n'_3=1.5250$).
Figure 18:
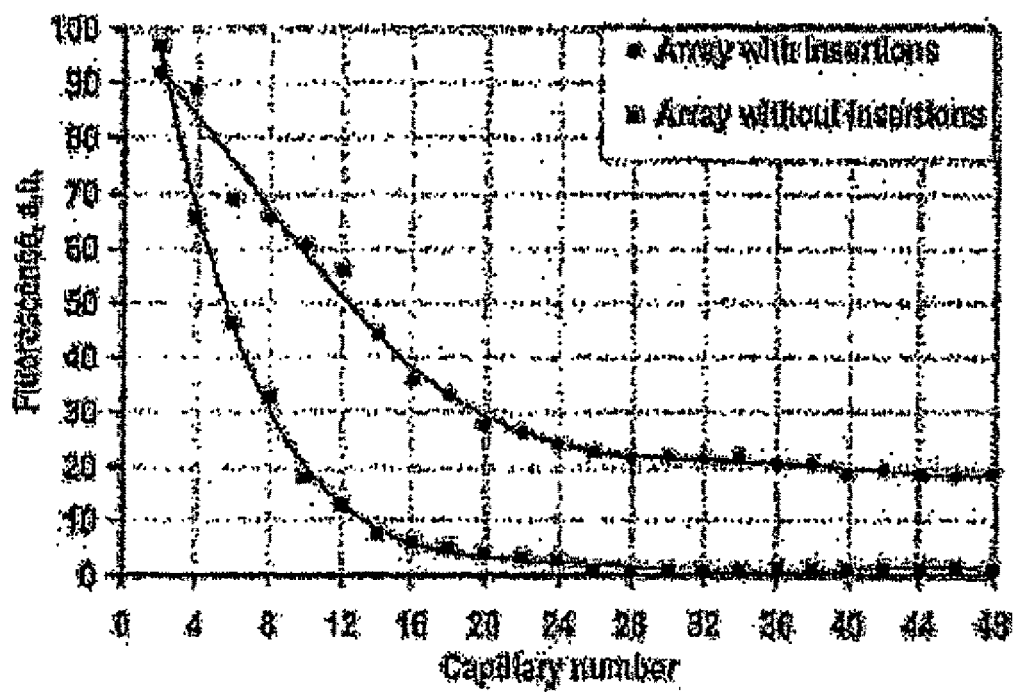
FIG. 18 shows the distribution of fluorescence intensity in a capillary array for a nonoptimum combination of refractive indices (array without insertions: $n_1=1.2925$, $n_2=1.4614$, $n_3=1.3830$; array with insertions: $n_1=1.4614$, $n_2=1.4614$, $n_3=1.3830$, $n'_3=1.5250$).

All refractive indices were measured using an Abbe refractometer (Model WY1A-52-975, Edmund Industrial Optics, NJ, USA). A summary for all refractive indices used in the experiment is shown in Table 1. Typical fluorescence images obtained from three 48-capillary arrays are shown in FIG. 16. Even visually one can see that in the array with nonoptimum capillary filling the fluorescence intensity decays quickly compared to the case of optimum refractive index of active capillaries. FIGS. 17, 18 present the distribution of fluorescence intensity obtained with the measurement setup shown in FIG. 5.

The experimental results are in good agreement with the results predicted by computer simulations. Indeed, in the case of optimum combination of refractive indices we have a difference of about 10% between distributions of fluorescence in 48-capillary arrays with and without composite insertion. However, for the nonoptimum combination of refractive indices there is a very significant difference in light transmittance between the two arrays. While the array without insertions practically loses its light guiding properties, the array with composite insertions still transmits nearly 20% of the optical power of the incident light beam. The obtained agreement between experimental data and results of the computer simulation demonstrate applicability of the developed computer simulation model to accurate description of multicapillary arrays with and without insertions. Practical implementation of 550-capillary array should easily exhibit the beam transmittance predicted by the computer simulation: our calculations showed that the acceptable divergence of the illumination beam was 10 mrad. Since typical beam divergence for commercial gas lasers is an order of magnitude smaller, we believe that the one-sided illumination of the 225-capillary array is feasible.

A structure of LMCA with composite insertions was analyzed, and it was found that using the dual-side illumination of the array one can uniformly and simultaneously irradiate as many as 550-capillaries. In comparison to conventional capillary arrays the structure has the following advantages:

(1) enables a significant increase in throughput of multilane DNA sequencers by simply increasing the number of simultaneously processed capillaries without significant changes in the instrument design;

(2) allows fabrication of multicapillary arrays capable of working with separation media having low refractive index (e.g., water);

(3) Does not add additional refractive index interface, thus providing very low reflection losses.

(4) Because composite insertions are formed by pieces of capillaries of the same outer diameter as working capillaries, it is possible to further improve light guiding properties of capillary arrays by varying the inner diameter of composite insertions; and (5) The calculations carried out are applicable to multilane arrays etched on glass chips if the etched channels are covered with a glass cover providing total internal reflection of the laser beam.

The use of nonsequencing capillaries as insertions does not affect the overall sequencing cost since the composite insertions proposed will be made of the same capillary tubing but will be short (~1 cm). Therefore, cost of the capillary tubing for an array with 50 cm capillaries will increase by only 2%. The required volume of the refractive index liquid for the whole array will be approximately 20 μL and has a negligible cost.

EXAMPLE 1

Figure 2A:
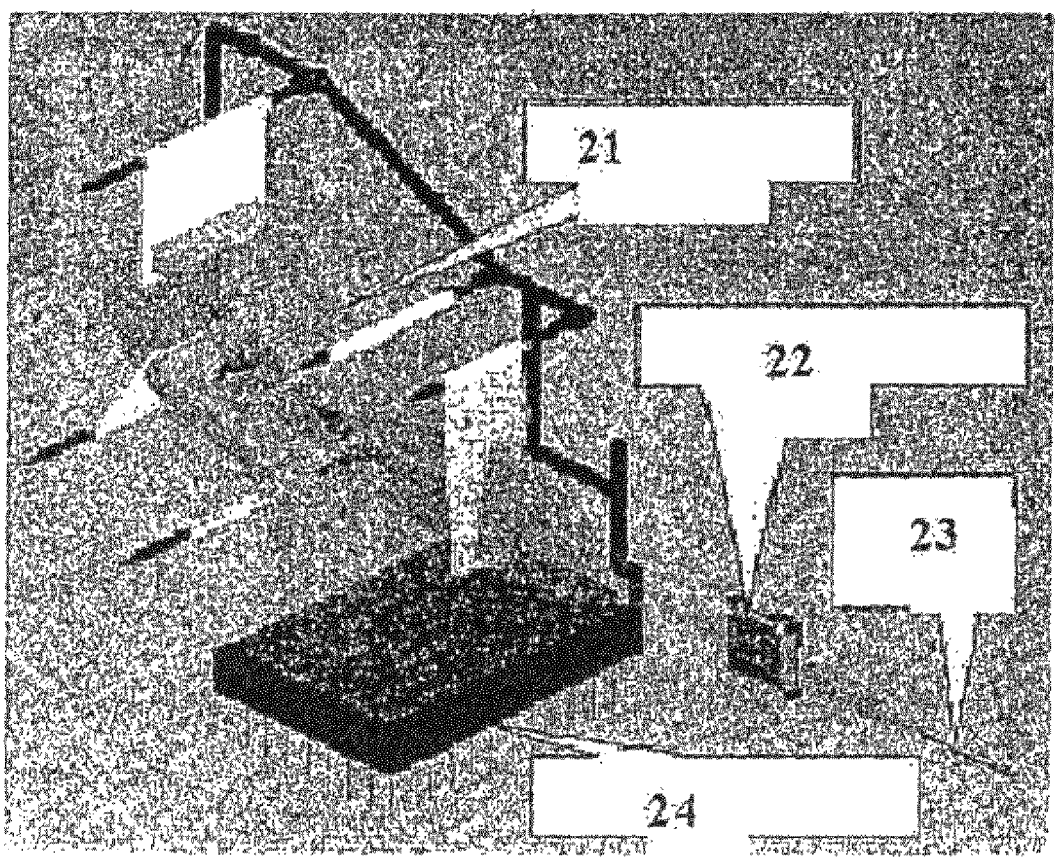
FIGS. 2A and 2B show a capillary array from Applied Biosystems. General view (2A top) and the array detection cell (2B bottom). Capillaries 21, Detection Cell 22, Array Inlet 23, Needles Plate 24, and Inlet for refill of matching liquid 25.
Figure 2B:
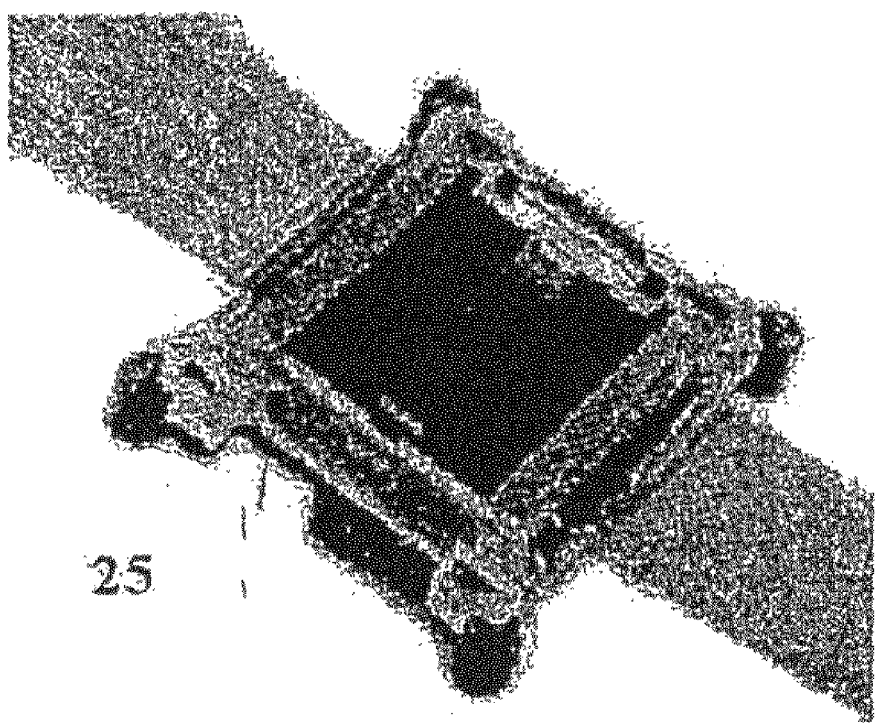

Commercially available 48- and 96-capillary arrays from ABI (Part nos. 4331250 and 4305787 from Applied Biosystems, Calif., USA) were used as a model system for our experimental studies (see FIG. 2). In both arrays the detection cell comprises capillaries aligned with silicon V-groves and immersed in a refractive index liquid with $n_1$=1.2925.

In our experiments the 48-capillary array represented a structure without insertions and the 96-capillary array was used to model a 48-capillary array with composite insertions. Odd-numbered capillaries of the 96-capillary array were filled with separation polymer POP-7 (ABI P/N 4352759) and even-numbered capillaries contained a refractive index liquid with a certain value of $n'_3$. The detection cell was modified to allow the replacement of the original refractive index liquid with a fused-silica matching liquid to exactly match the refractive index of capillary walls. Since the period of the 96-capillary array is equal to the outer diameter of the capillary (150 μm), and the 48-capillary array has a period equal to twice the outer diameter, we were able to directly compare the structures with and without composite insertions.

Figure 3:
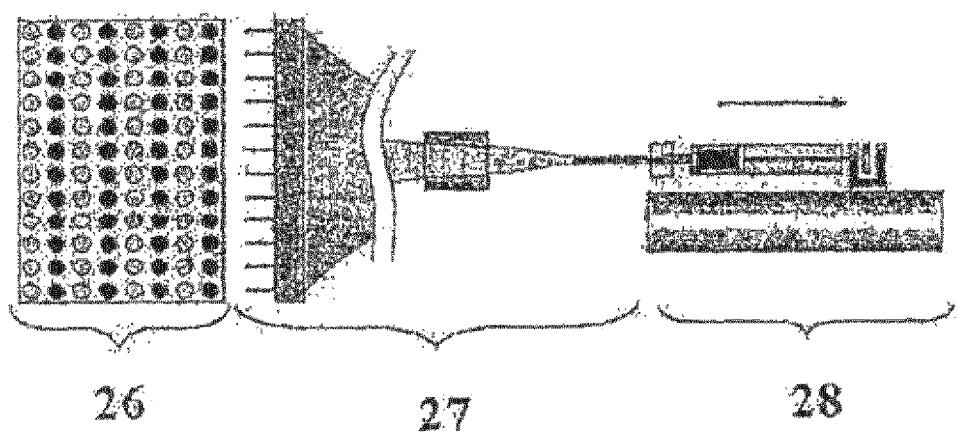
FIG. 3 shows a schematic of a setup for filling the 96-capillary array with the arrow in the schematic showing the direction of flow. Ninety-six Well Plate 26, Capillary Array 27, Syringe Infusion Pump 28.

Prior to filling, the arrays were cleaned by washing with 1% Liqui-Nox liquid detergent solution, followed by repeated washing with distilled water, and dried by air, all pressed via a syringe tightly coupled to the inlet. Next, the capillaries were filled with corresponding liquids. In order to measure propagation of the laser beam through arrays, we filled active capillaries of the arrays with a mix of POP-7 polymer and fluorescent dye (TAMRA). The 48-capillary array was filled with the gel mix through a 0.1 mL syringe coupled to the array inlet. A special setup (FIG. 3) was built for filling the 96-capillary array so that it could model the 48-capillary array with composite insertions. The appropriate liquids were drawn into the array through the needle ends of individual capillaries. The POP-7 polymer-dye mix was placed in the odd-numbered columns of the 96-well plate, and a refractive index liquid with $n'_3=1.5250$ (A-1.525 Certified Refractive index liquid, Cargille Labs) was placed in even-numbered columns of the plate. The plate was sealed with septa, and the ends of the capillaries were immersed in corresponding wells of the tray. The array filling was performed using negative pressure applied to the inlet end of the array with a programmable syringe infusion pump (Model KDS220, KD Scientific, MA., USA). In order to ensure bubble-free filling of the array, the filling process was performed at a low rate. Bubble free filling of the array detection cell was controlled during the filling process using a setup shown in FIG. 4.

Original refractive index liquid was removed from the cell, and the cell was washed with alcohol, dried, and filled with the refractive index liquid of $n_1=1.4614$ (Code 50350 fused-silica matching liquid, Cargille Labs) which exactly matched the refractive index of the capillary walls. To ensure uniform filling, the detection cell was controlled through a microscope at every step of the filling process.

Figure 4:
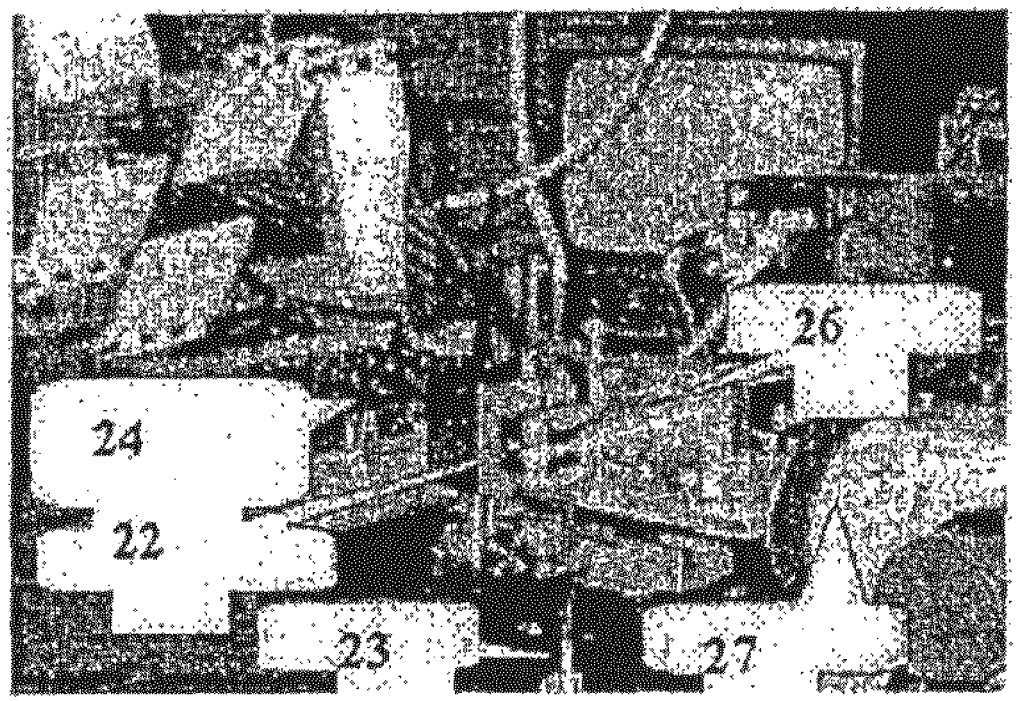
FIG. 4 shows an array imaging setup. Detection Cell 22, Array Inlet 23, Needles Plate 24, Laser Head 26, and Microscope 27.
Figure 5:
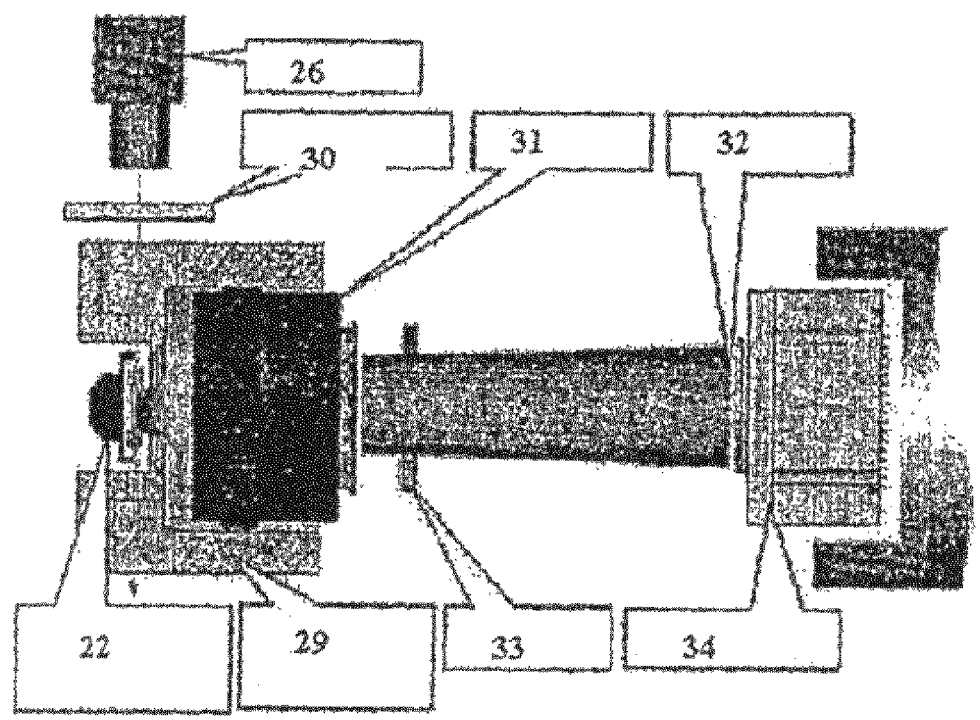
FIG. 5 shows a schematic of the experimental setup for measurement of the light propagation through multicapillary arrays. Detection Cell 22, Laser Head 26, Optical Head Assembly 29, Neutral Filter 30, Canon Lens 31, Array Image 32, Step Filter 33, and PMT Assembly 34.
Figure 6:
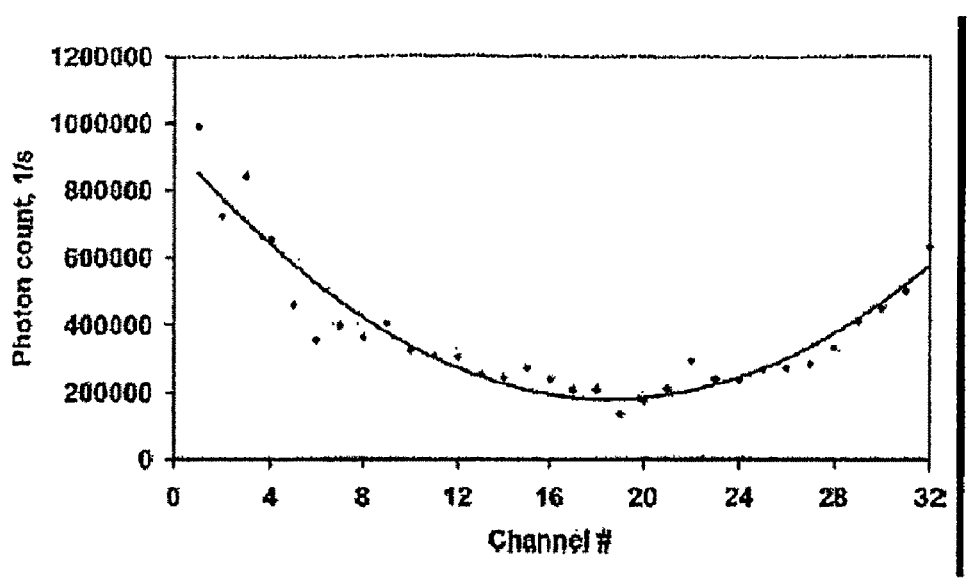
FIG. 6 shows a profile of the collection efficiency of the measurement setup.
Figure 19:
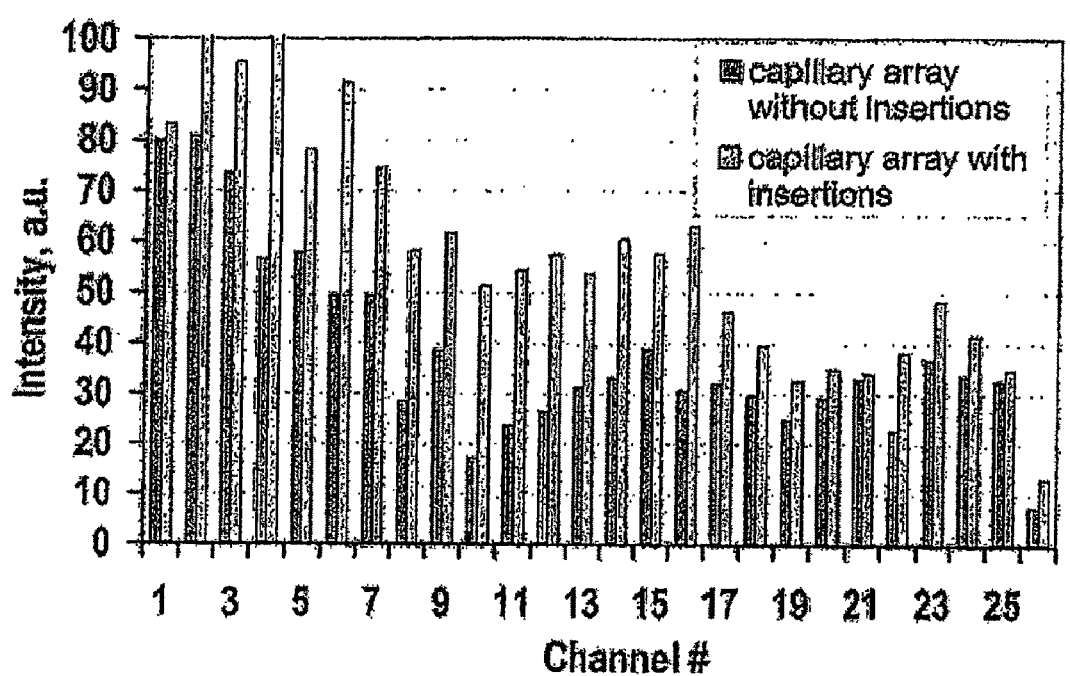
FIG. 19 shows the fluorescence intensity distribution in a capillary array for an optimum combination of parameter values (array without insertions: $n_1=1.2925$, $n_2=1.4614$, $n_3=1.40$; array with insertions: $n_1=1.4614$, $n_2=1.4614$, $n_3=1.40$, $n'_3=1.525$).
Figure 20:
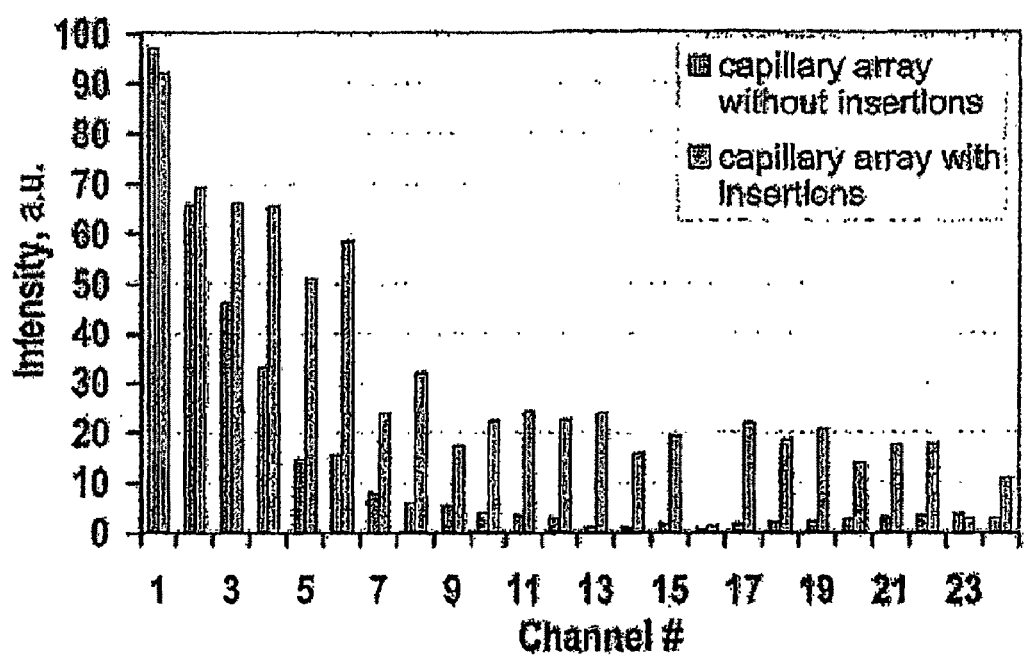
FIG. 20 shows a fluorescence intensity distribution in a capillary array for a non-optimum combination of parameter values (array without insertions: $n_1=1.2925$, $n_2=1.4614$, $n_3=1.383$; array with insertions: $n_1=1.4614$, $n_2=1.4614$, $n_3=1.383$, $n'_3=1.525$).
Figure 21:
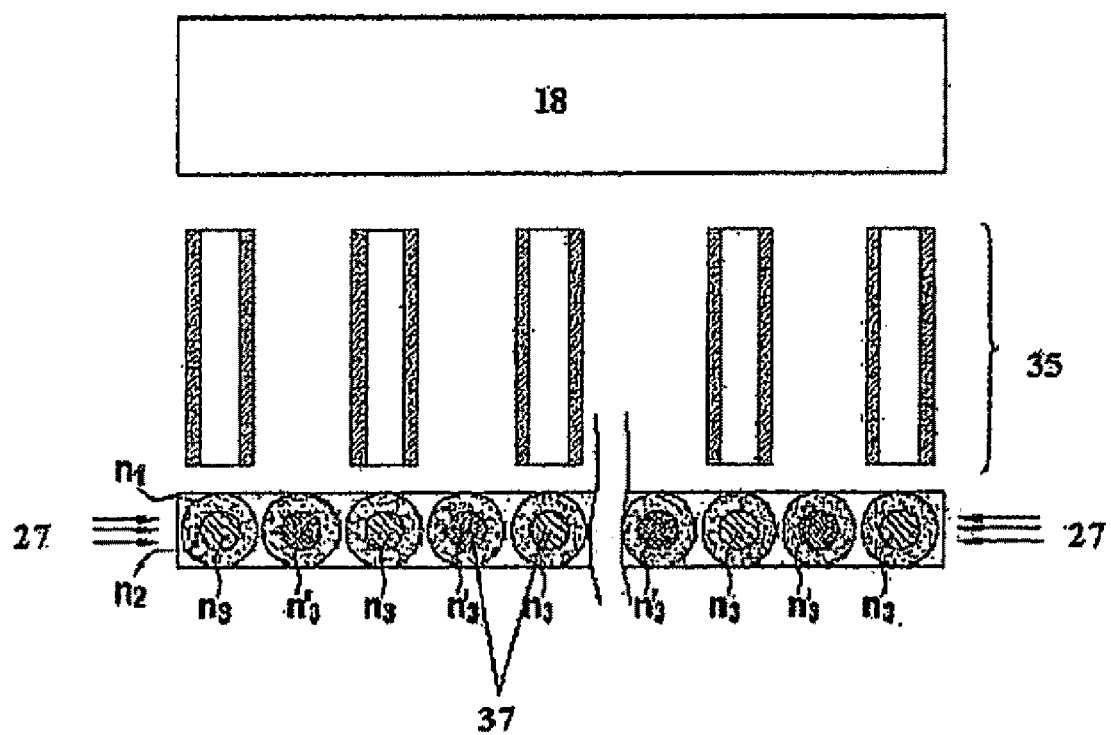
FIG. 21 shows a laser illumination and fluorescence collection system comprising a capillary array 27 with composite insertions 37, image transmitting fiber array 35, and multi-channel photodetector 18. The arrows show the direction of the applied laser beams.
Figure 22:
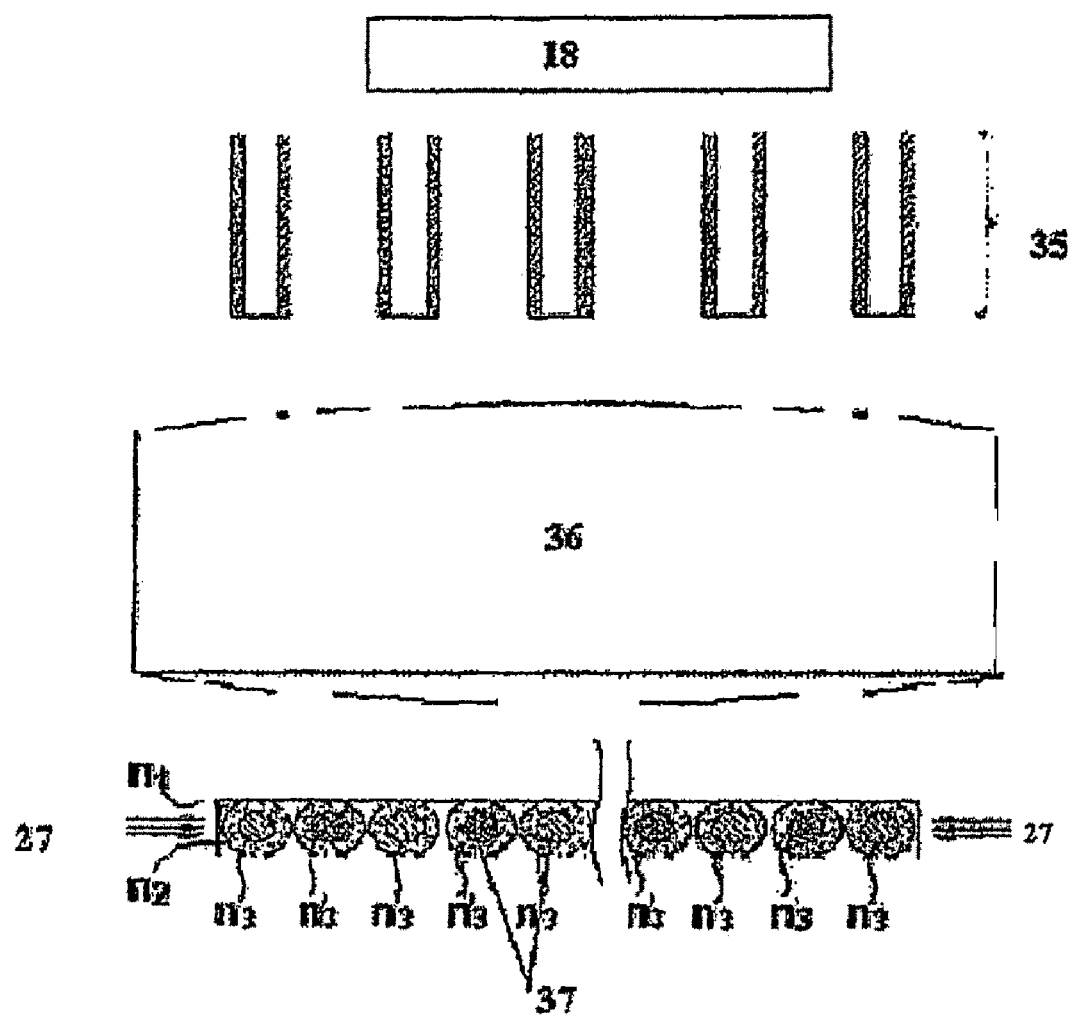
FIG. 22 shows a laser illumination and fluorescence collection system comprising a capillary array 27 with composite insertions 37, image transmitting fiber array, high-aperture projection optics 36, and multi-channel photodetector 18. The arrows show the direction of the applied laser beams.
Figure 23:
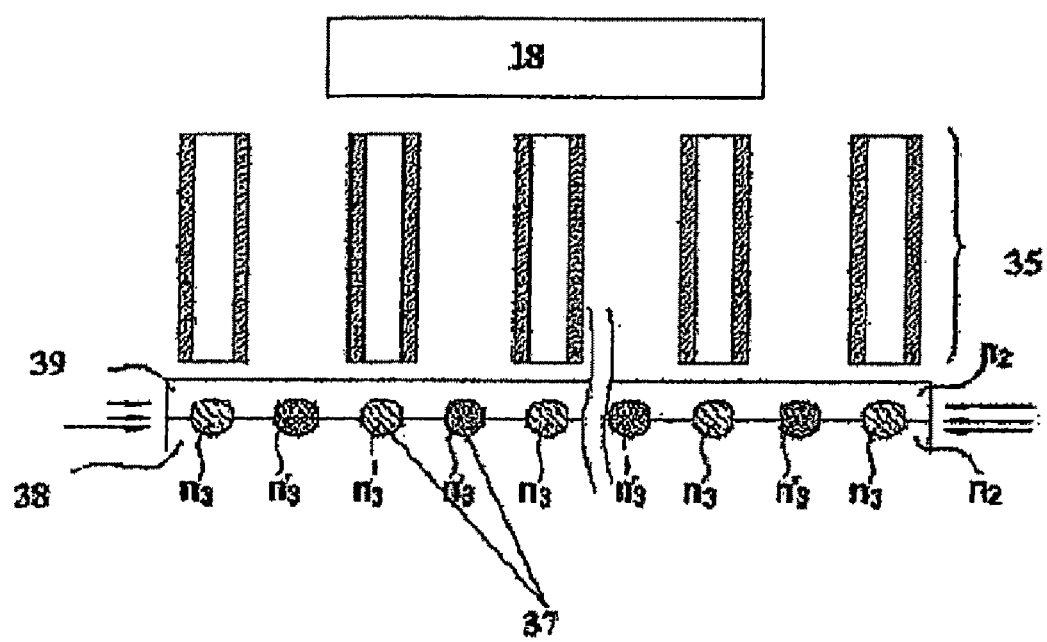
FIG. 23 shows a laser illumination and fluorescence collection system comprising etched-on-glass chip capillary array 38 with composite insertions 37, replicated cover of glass chip 39, image transmitting fiber array 35, and multi-channel photodetector 18. The arrows show the direction of the applied laser beams.
Figure 24:
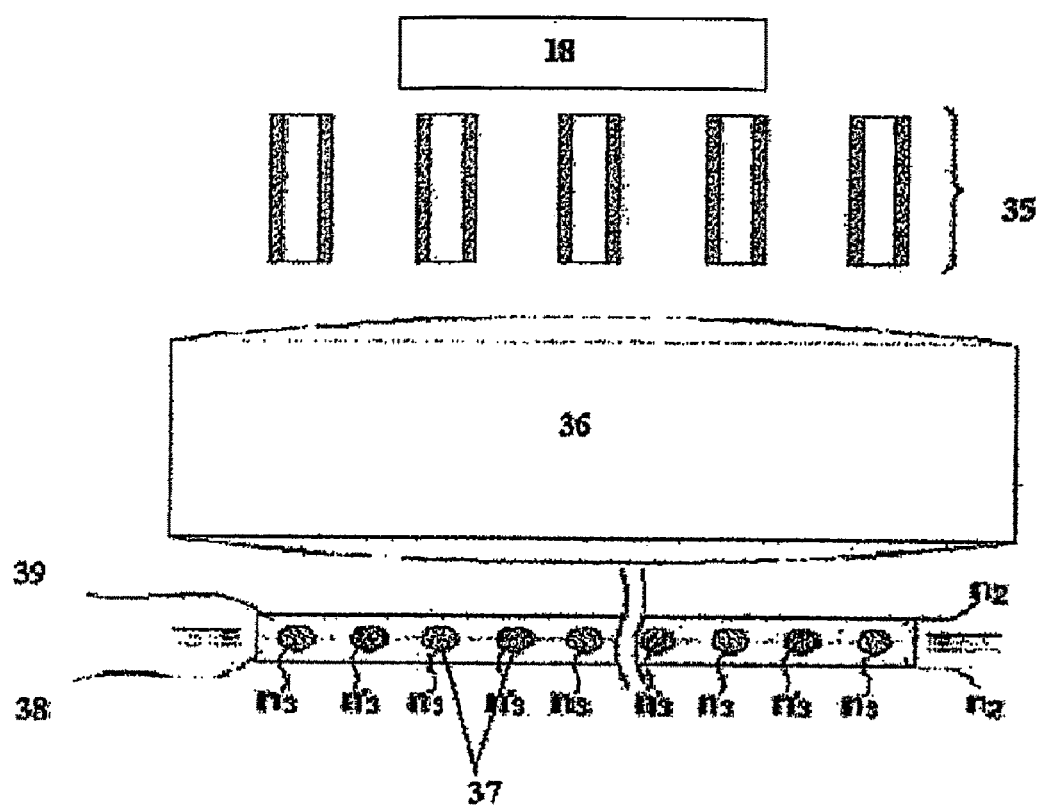
FIG. 24 shows a laser illumination and fluorescence collection system comprising etched-on-glass-chip capillary array 38 with composite insertions 37, replicated cover of glass chip 39, image transmitting fiber array 35, high-aperture projection optics 36, and multi-channel photodetector 18. The arrows show the direction of the applied laser beams.
Figure 25:
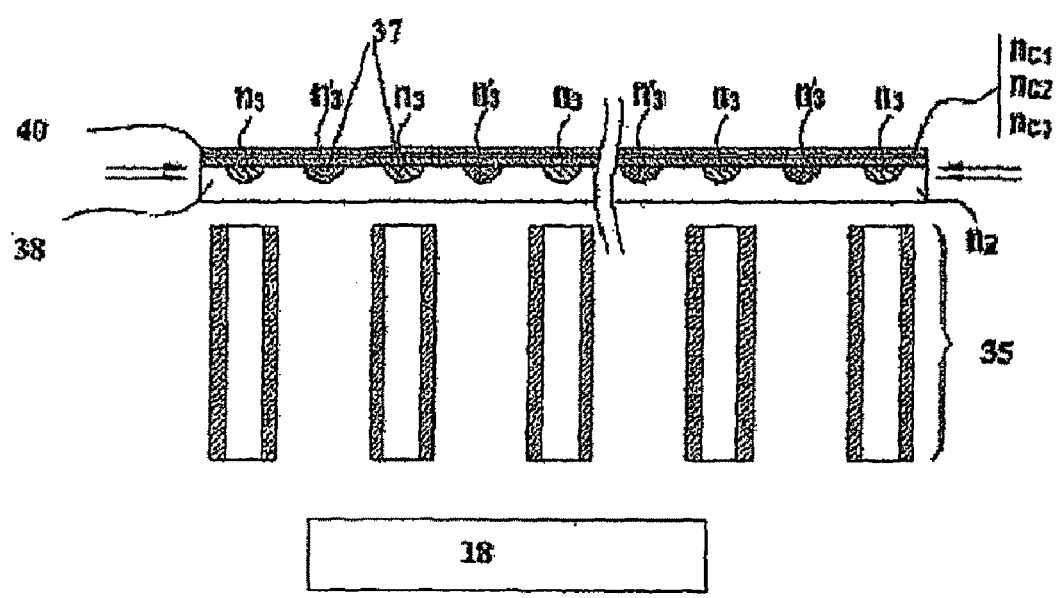
FIG. 25 shows a laser illumination and fluorescence collection system comprising etched-on-glass-chip capillary array 38 with composite insertions 37, sandwiched cover of glass chip 40, image transmitting fiber array 35, and multi-channel photodetector 18. The arrows show the direction of the applied laser beams.
Figure 26:
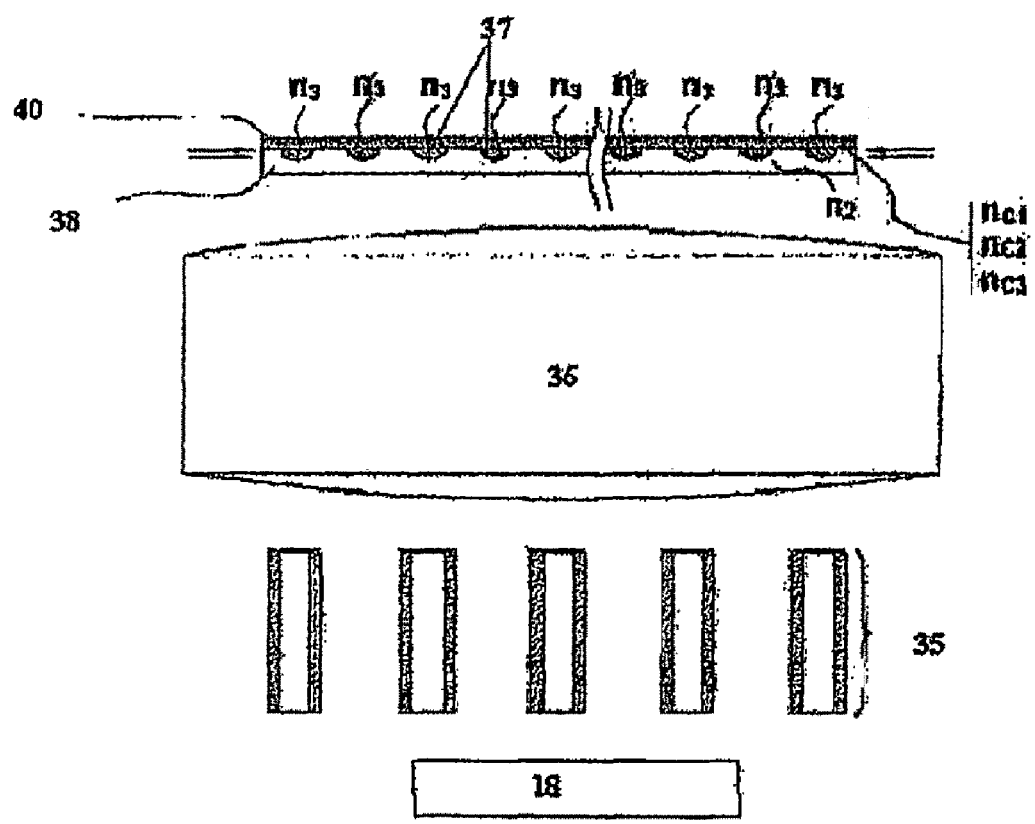
FIG. 26 shows a laser illumination and fluorescence collection system comprising etched-on-glass-chip capillary array 38 with composite insertions 37, sandwiched cover of glass chip 40, image transmitting fiber array 35, high-aperture projection optics 36, and multi-channel photodetector 18. The arrows show the direction of the applied laser beams.
Figure 27:
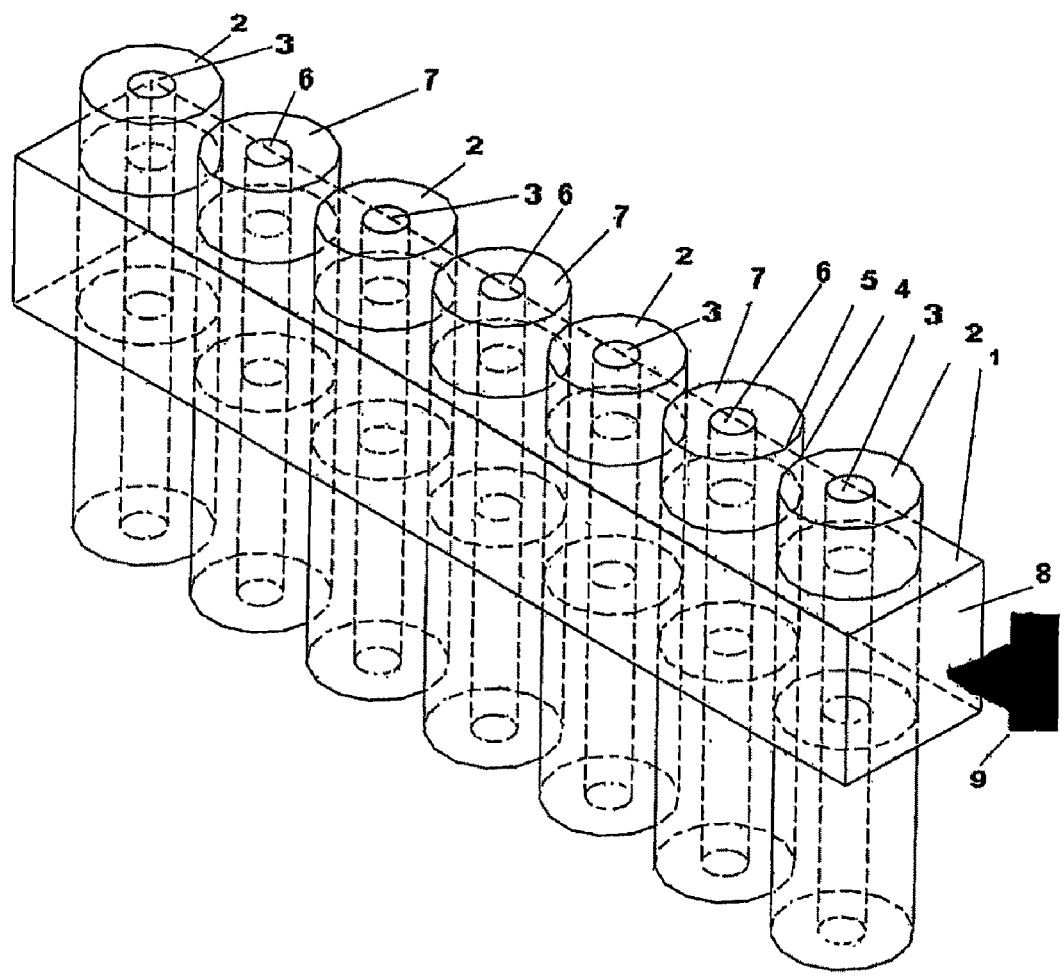
FIG. 27 shows a device comprising: a first plurality of capillary tubes comprised of a quartz material configured in an alignment, a first medium inside said plurality of capillary tubes, which medium is a polymer separation material, a second plurality of capillary tubes with a second focusing medium having a refractive index greater than the first medium, a compartment containing the capillary tubes, a source of electromagnetic radiation such as a laser, and a third medium inside the compartment that surrounds the capillary tubes, which third medium is preferably a liquid with a refractive index identical to quartz; with a short distance between the outside of a first capillary tube and the outside of a second capillary tube adjacent the first capillary tube.
Figure 28:
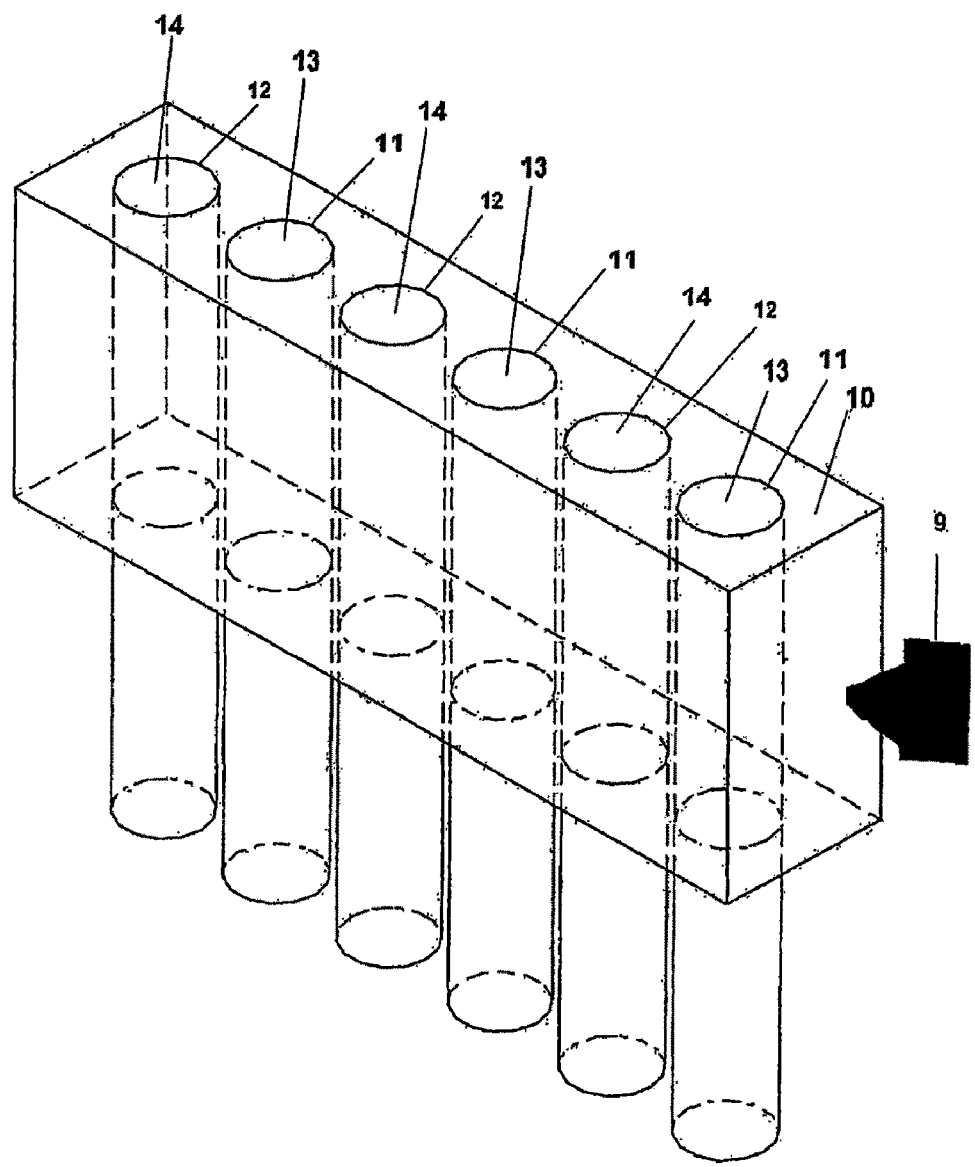
FIG. 28 shows a device comprising a transparent material comprising a plurality of channels filled with a first transparent medium and a second plurality of channels filled with a second medium; a laser wherein said first and second plurality of channels are in an alignment parallel to each other and perpendicular to a laser beam.
Figure 29:
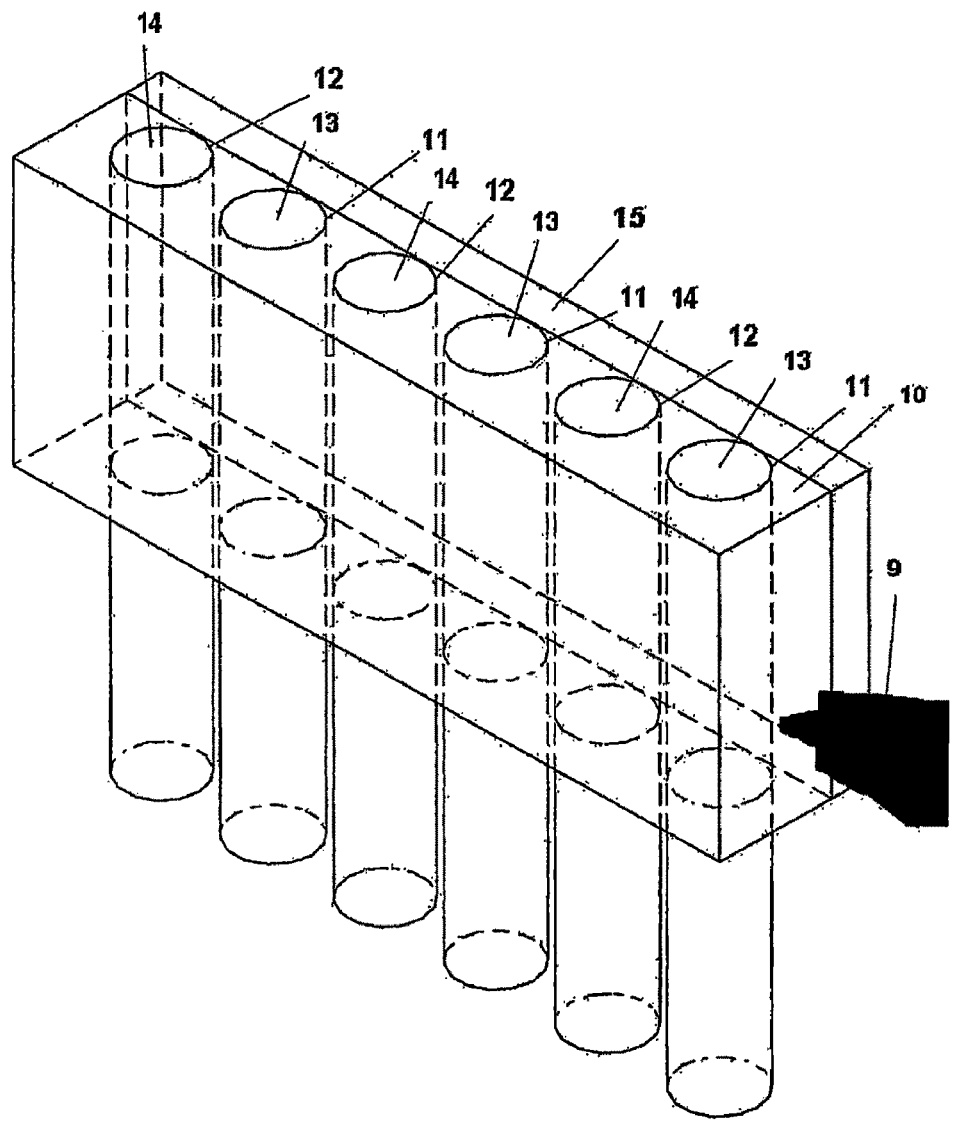
FIG. 29 shows a device comprising: a transparent material with a first plurality of channels filled with a first transparent medium and a second plurality of channels (12) filled with a second medium; a laser configured to produce a light beam; and a reflective surface.
Figure 30:
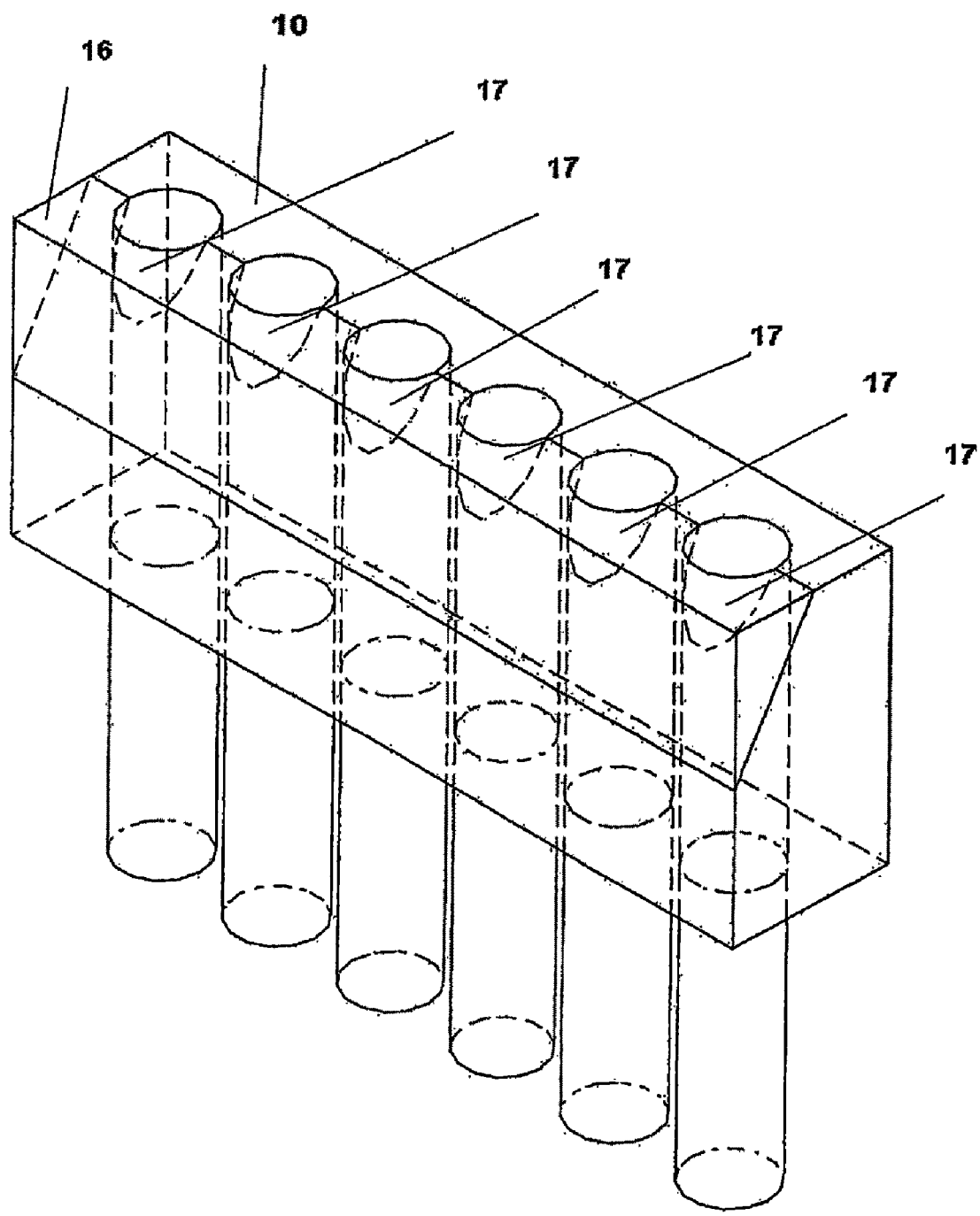
FIG. 30 shows a device comprising: a transparent material comprising a first plurality of channels filled with a first transparent medium and a second plurality of channels filled with a second medium; and a cover comprising a plurality of reflective surfaces.
Figure 31:
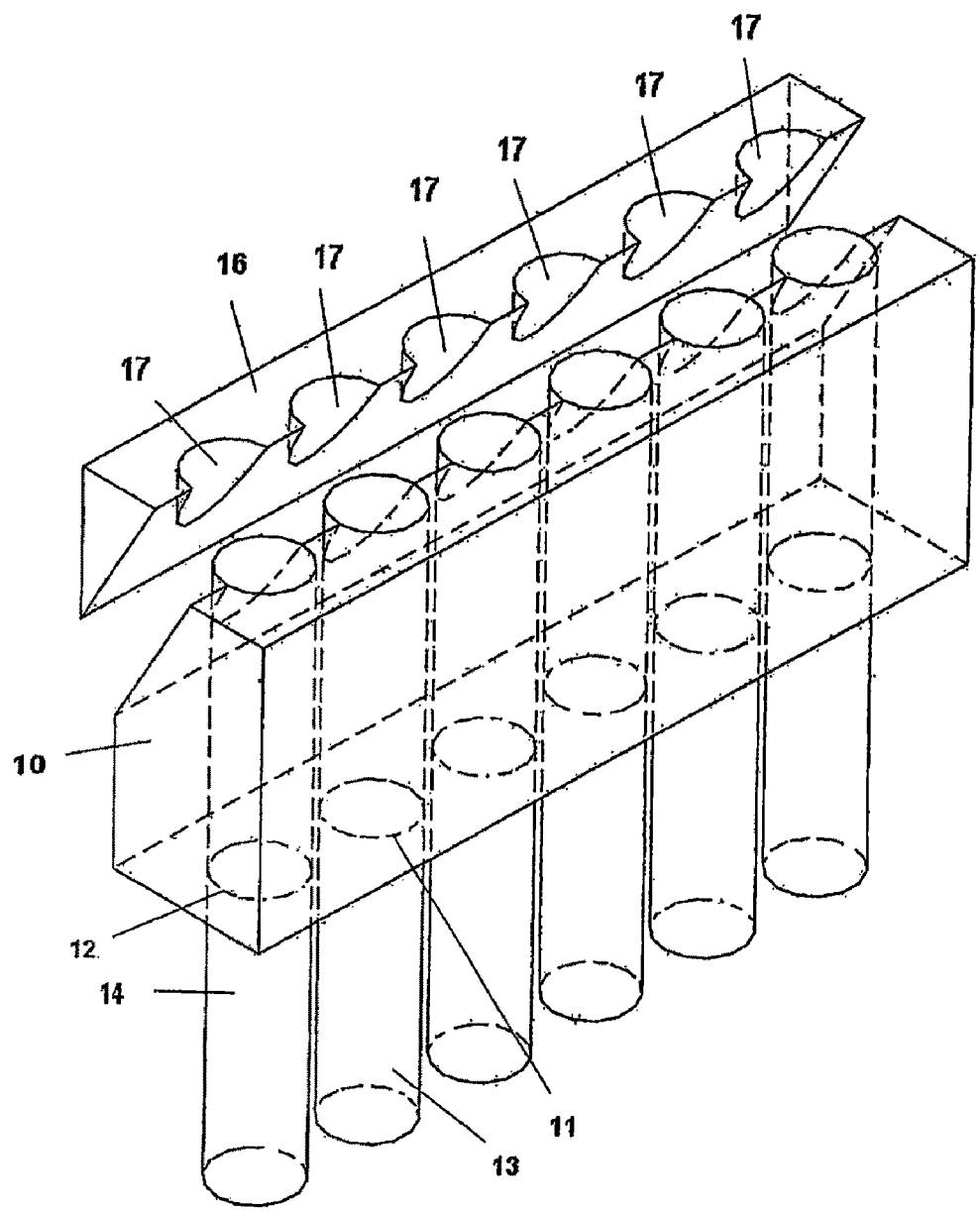
FIG. 31 shows another view of the device in FIG. 30 wherein the cover is removed.
Figure 32:
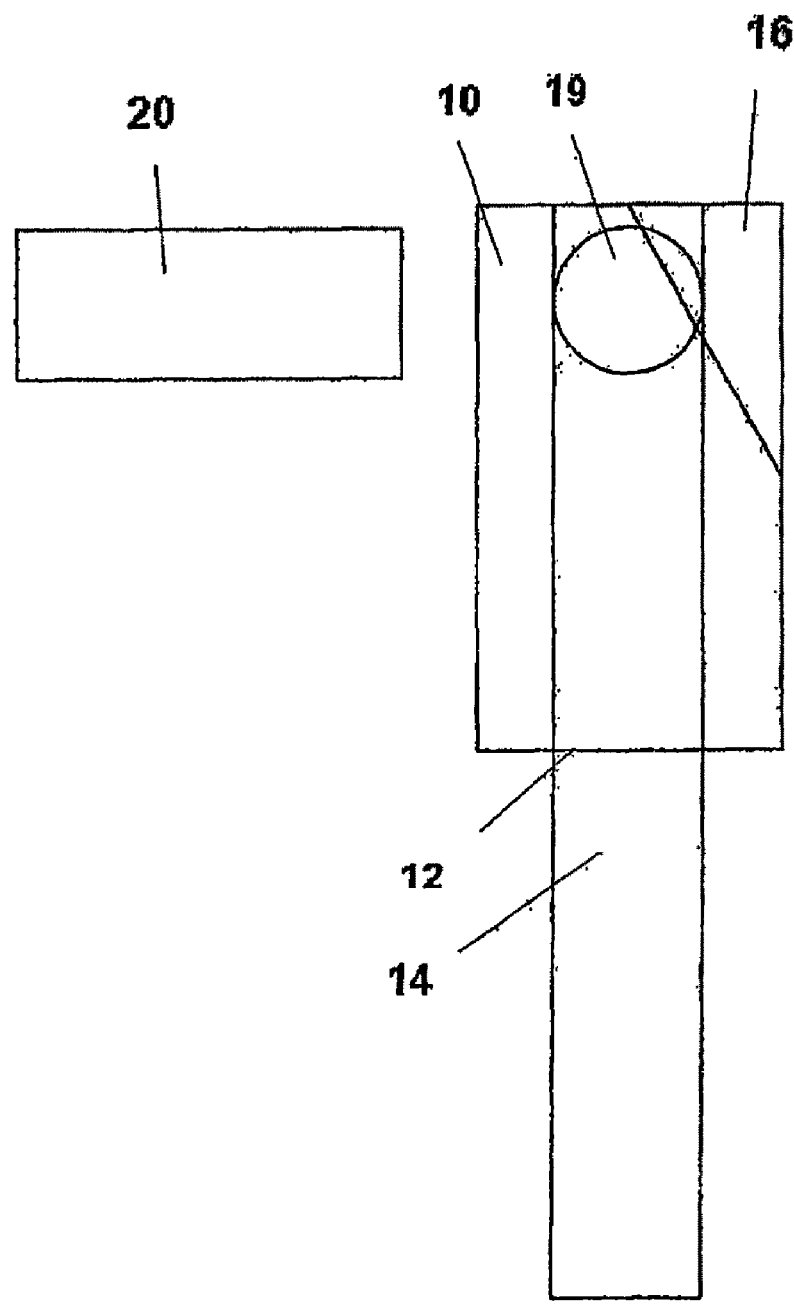
FIG. 32 shows another view of the device of FIG. 30 illustrating the path of a laser illumination beam and a multipixel photodetector.

A setup for imaging of the light propagation through the array is shown in FIG. 4. FIG. 5 presents a schematic of the setup for the light propagation measurement through multi-capillary arrays. The setup operates as follows: the array detection cell is inserted in the Optical Head Assembly, which holds the detection cell of the array in a precisely specified, fixed position, holds the laser beam adjusting system, and has mounts for the collecting lens adjustment system. The laser beam illuminates the array from the side and excites the fluorescence in the capillaries of the array. The fluorescence image is captured by a Canon lens (EF 50 mm f/1.4 USM, Canon USA, N.Y., USA), magnified, passed through the laser rejection filter (AELP540, Omega Optical, VT., USA) and projected onto the photoreceiving bars of a 32-channel single photon PMT (H7260, Hamamatsu Photonics, Japan). For the illumination of the capillary array we used 25 mW single mode Nd-YAG laser (532 nm, 300 μm beam diameter, Crystal Lasers, N.J., USA). In order to avoid the fluorescence bleaching inside working capillaries and to ensure that the photomultiplier tube (PMI) works in the linear regime, a neutral 3 OD filter was used to reduce laser power passing through the array. All dimensions of the measurement system Were chosen to achieve image magnification equal to 1.63. In this case we projected the image of 48 working capillaries onto 24 bars of the PMT. Data from the PMT was collected, recorded, and visualized in real time by our data recording software. Before starting data collection, we calibrated our optical system by illuminating a cuvette with $10^{-6}$ M water solution of TAMRA. The measured fluorescence profile is shown in FIG. 6. After aligning and calibrating the optical system, the 48-and 96-capillary arrays were inserted in the optical reading head and fluorescence signals were measured and recorded. FIGS. 19 and 20 present distribution of fluorescence intensity obtained with the measurement setup shown in FIG. 4.

The invention claimed is:

1. A device comprising:
   i) a laser configured to produce a light beam,
   ii) a transparent material having a first refractive index comprising
      a) a first plurality of channels filled with a first transparent medium having a second refractive index and
      b) a second plurality of channels filled with a second medium having a third refractive index;
   wherein said first and second plurality of channels are commingled in an alignment parallel to each other and perpendicular to said beam;
   wherein said third refractive index is greater than said first refractive index and said third refractive index is greater than said second refractive index.

2. The device of claim 1, wherein the value of said third refractive index minus said first refractive index is equal to the value of said third refractive index minus said first refractive index.

3. The device of claim 1, wherein said third refractive index is greater than fused silica.

4. A device comprising:
   a first plurality of capillary tubes comprised of a first material having a first refractive index,
   a first medium having a second refractive index, said first medium disposed inside said first plurality of capillary tubes,
   a second plurality of capillary tubes comprised of a second material having a third refractive index,
   a second medium having a fourth refractive index, said second medium disposed inside said second plurality of capillary tubes,
   a compartment,
   a source of electromagnetic radiation, and
   a third medium having a fifth refractive index;
   wherein at least a portion of said first and second plurality of capillary tubes are contained in said compartment and said third medium is configured to surround at least a portion of the outside of said first and second plurality of capillary tubes;
   wherein said first plurality of capillary tubes and said second plurality of capillary tubes are configured in an alignment such that said electromagnetic radiation travels through said capillary tubes;
   wherein said first and third refractive index are equal; and
   wherein said fourth refractive index is greater than said first, third, and fifth refractive index.

5. The device in claim 4, wherein said fifth refractive index is greater than 1.33.

6. The device in claim 4, wherein said second refractive index is less that said first, third, and fifth refractive index.

7. The device in claim 4, wherein said first and second material are both fused silica.

8. The device in claim 4, wherein said first, third, and fifth refractive index are equal.

9. The device in claim 4, wherein said second refractive index is between 1.33 and 1.44, and said fourth refractive index is between 1.48 and 1.70.

10. The device in claim 4, wherein the distance between the outside of a member of said first plurality of capillary tubes adjacent to the outside of a member of said second plurality of capillary tubes is less than 50 micrometers.

11. The device in claim 4, wherein said electromagnetic radiation is directed in a path less than the width of the inner diameter of a member of said first and second plurality of capillary tubes.

12. The device in claim 4, wherein deviations in the alignment between adjacent capillary tubes are less than 1 micrometer.

13. The device in claim 4, wherein deviations in the period between adjacent capillary tubes are less than 9 micrometers.

14. A device comprising:
   i) a laser configured to produce a light beam;
   ii) a transparent material having a first refractive index comprising
      a) a first plurality of channels filled with a first transparent medium having a second refractive index and
      b) a second plurality of channels filled with a second medium having a third refractive index;
   wherein said first and second plurality of channels are in an alignment parallel to each other and perpendicular to said light beam;
   iii) a reflective surface; and
   iv) a multichannel photodetector having a plurality of waveguides.

15. The device of claim 14, wherein said reflective surface is configured to reflect scattered light in the direction of a central axis of a channel.

16. The device of claim 14, wherein said reflective surface is a mirror.

17. The device of claim 14, wherein said first medium permits a fluid to flow therethrough.

18. The device of claim 14, wherein said third refractive index is greater than said first refractive index and said third refractive index is greater than said second refractive index.

19. The device of claim 14, wherein the absolute value of said third refractive index minus said first refractive index is equal to the absolute value of said third refractive index minus said first refractive index.

20. The device of claim 14, wherein said third refractive index is greater than fused silica.

21. A linear multi-capillary array comprising:
   a plurality of active capillaries;
   a plurality of composite optical insertions;
   wherein said active capillaries and said composite optical insertions comprise at least two media with different refractive indices
   wherein said plurality of composite optical insertions and the active capillaries are commingled,
   wherein the refractive indices of said active capillaries, said composite insertions and a medium surrounding a detection zone of the linear multi-capillary array are selected so that they provide maximum transmission of the laser beam through the linear multi-capillary array.

22. A method of constructing a linear multicapillary array comprising:
   providing
      i) a plurality of active capillaries and a plurality of composite optical insertions, wherein said plurality of active capillaries and said composite optical insertions comprise at least two media with different refractive indices wherein said plurality of composite optical inserts and the active capillaries are commingled and
      ii) a computer;
   programming said computer to provide varied parameter values associated with formula (1) and formula (2)
   determining transmittance in relation to said varied parameter values that provide a desired transmittance; and
   constructing a linear multicapillary array configured to provide said desired transmittance.

23. Laser illumination and fluorescence collection system comprising a capillary array with composite insertions, image transmitting fiber array, and multi-channel photodetector.

24. Laser illumination and fluorescence collection system of claim 23 further comprising high-aperture projection optics.

25. A chip of a refractive index $n_2$ configured such that said chip contains working channels filled with polymer having a refractive index $n_3$ alternated by channels filled with medium of refractive index $n'_3$; wherein $n'_3$ is greater than $n_2$ and $n'_3$ is greater than $n_3$.

26. Array on chip of claim 25 in which the absolute value of $n'_3$ minus $n_2$ is equal to the absolute value of $n_3$ minus $n_2$.

27. Array on chip of claim 25 having a cover.

28. Array on chip of claim 27 having a cover configured such that said cover forms channels together with channels on said chip.

29. Array on chip of claim 28 wherein the cover comprises a material that provides internal reflection of the laser illumination beam from any point on the surface of the array.

30. Array on chip of claim 29 wherein the cover comprises at least two layers of different materials.

31. Array on chip of claim 27, wherein the cover comprises a mirror.

32. Array on chip of claim 31 wherein the cover comprises a dielectric mirror.

* * * * *